US009445912B2

(12) United States Patent
Oster

(10) Patent No.: US 9,445,912 B2
(45) Date of Patent: Sep. 20, 2016

(54) PROSTHESIS FOR ARTHRODHESIS

(75) Inventor: Lars Oster, Lidkoping (SE)

(73) Assignee: Swemac Innovation AB (SE)

( * ) Notice: Subject to any disclaimer, the term of this patent is extended or adjusted under 35 U.S.C. 154(b) by 30 days.

(21) Appl. No.: 13/984,111

(22) PCT Filed: Dec. 27, 2011

(86) PCT No.: PCT/SE2011/051594
§ 371 (c)(1), (2), (4) Date: Sep. 23, 2013

(87) PCT Pub. No.: WO2012/121640
PCT Pub. Date: Sep. 13, 2012

(65) Prior Publication Data
US 2014/0018930 A1 Jan. 16, 2014

(30) Foreign Application Priority Data
Mar. 4, 2011 (SE) ...................................... 1150197

(51) Int. Cl.
*A61F 2/42* (2006.01)
*A61B 17/72* (2006.01)
(Continued)

(52) U.S. Cl.
CPC ......... *A61F 2/4261* (2013.01); *A61B 17/7291* (2013.01); *A61B 17/1725* (2013.01);
(Continued)

(58) Field of Classification Search
CPC ..................... A61F 2/4261; A61F 2002/4264; A61B 17/7291
USPC ............................. 623/21.11, 21.12; 606/62
See application file for complete search history.

(56) References Cited

U.S. PATENT DOCUMENTS 4,304,011 A 12/1981 Whelan, III
5,147,386 A 9/1992 Carignan et al.
(Continued)

FOREIGN PATENT DOCUMENTS

| | | |
|---|---|---|
| DE | 3347055 | 7/1985 |
| FR | 2692776 | 12/1993 |
| SE | 528 545 | 12/2006 |
| WO | 91/04718 | 4/1991 |
| WO | 2010/096724 | 8/2010 |

*Primary Examiner* — David H. Willse
*Assistant Examiner* — Javier Blanco
(74) *Attorney, Agent, or Firm* — Tarolli, Sundheim, Covell & Tummino LLP

(57) ABSTRACT

A prosthesis for primary artrodhesis can be used for artroplasty and a prosthesis for artroplasty comprises members for artrodhesis. The prosthesis (1*b*) for primary artrodhesis comprises a locking member (33*b*) with an attachment portion (16*b*) which is insertable into a hole (8*b*) in a first attachment member (4*b*) of the prosthesis for location of the locking member therein, and a lockable member (34*b*) integral with a second attachment member (5*b*) of the prosthesis. The lockable member (34*b*) is configured for adjustable setting thereof relative to the locking member (33*b*) and for fixation thereof, in set position, to the locking member. Alternatively, the lockable member comprises an attachment portion which is insertable into a hole in the second attachment member for location of the lockable member therein. At the prosthesis for artroplasty, the hole in the first screw-like attachment member is partly configured to define a press fit with an attachment pin of a socket member and partly threaded to permit, after removal of the socket member, during artrodhesis, securing by screwing in the hole of the locking member for cooperation with a lockable member which is configured for adjustable setting thereof relative to the locking member and for fixation thereof, in set position, to the locking member.

12 Claims, 20 Drawing Sheets

(51) Int. Cl.
*A61F 2/30* (2006.01)
*A61F 2/46* (2006.01)
*A61B 17/17* (2006.01)
*A61B 17/80* (2006.01)

(52) U.S. Cl.
CPC ....... *A61B 17/80* (2013.01); *A61F 2002/3085* (2013.01); *A61F 2002/30332* (2013.01); *A61F 2002/30405* (2013.01); *A61F 2002/30433* (2013.01); *A61F 2002/30471* (2013.01); *A61F 2002/30494* (2013.01); *A61F 2002/30507* (2013.01); *A61F 2002/30538* (2013.01); *A61F 2002/30578* (2013.01); *A61F 2002/30607* (2013.01); *A61F 2002/30614* (2013.01); *A61F 2002/30622* (2013.01); *A61F 2002/4264* (2013.01); *A61F 2002/4677* (2013.01)

(56) References Cited

U.S. PATENT DOCUMENTS

| | | | | |
|---|---|---|---|---|
| 5,167,661 | A | 12/1992 | Wagenknecht | |
| 5,405,347 | A * | 4/1995 | Lee et al. | 606/54 |
| 6,099,571 | A | 8/2000 | Knapp | |
| 6,475,242 | B1 * | 11/2002 | Bramlet | 623/21.11 |
| 7,837,738 | B2 | 11/2010 | Reigstad et al. | |
| 2004/0153073 | A1 | 8/2004 | Orbay | |
| 2007/0078519 | A1 | 4/2007 | Klotz | |
| 2008/0065224 | A1 | 3/2008 | Reigstad et al. | |
| 2009/0171463 | A1 | 7/2009 | Brehm | |
| 2010/0130978 | A1 | 5/2010 | Orbay et al. | |
| 2011/0160728 | A1 * | 6/2011 | Blitz et al. | 606/64 |

* cited by examiner 28
27
5
26
24
13
3
20
9
19
12
1
18
7
15
6
2
16
10
17
8
14
11
4
25

32
31
30
25
23
5
28
27

4
25
22
21
5
27
23
28

28a
5a
35a
26a
36a
3a
27a
34a
24a
1a
44a
43a
33a
2a
4a
25a 5a
35a
3a
36a
1a
44a
34a
33a
43a
40a
37a
2a
4a 5a
3a
36a
35a
1a
44a
43a
33a
40a
37a
45a
47a
34a
46a
16a
38a
8a
39a
17a
14a
2a
4a 33a
42a
40a
42a
41a
37a
16a
38a
16a 28b
36b
27b
5b
3b
26b
35b
34b
44b
1b
43b
24b
33b
2b
4b
25b 5b
36b
3b
1b
44b
42b
43b
33b
37b
40b
41b
47b
45b
34b
46b
35b
16b
38b
8b
17b
39b
14b
2b
4b 5b
3b
35b
34b
47b
45b
46b 28c
5c
27c
26c
3c
24c
44c
1c
33c
43c
34c
2c
4c
25c 1c
5c
3c
44c
43c
33c
37c
40c
34c
2c
4c 5c
3c
1c
9c
42c
44c
47c
34c
41c
37c
19c
43c
40c
33c
45c
20c
46c
16c
38c
17c
2c
8c
39c
4c
14c 5d
3d
19d
53d
43d
33d
37d
48d
9d
51d
52d
34d
20d
19d
53d
45d
43d
38d
16d
39d
17d
2d
8d
4d
14d
1d 1d
3d
34d
19d
5d
9d
45d
53d
51d
52d
49d
39d
37d
38d
16d
50d
54d
4d
33d
43d
2d

PROSTHESIS FOR ARTHRODHESIS

RELATED APPLICATIONS

This application corresponds to PCT/SE2011/051594, filed Dec. 27, 2011, which claims the benefit of Swedish Application No. 1150197-0, filed Mar. 4, 2011, the subject matter, of which are incorporated herein by reference in their entirety.

TECHNICAL FIELD

The present invention relates to a prosthesis for artrodhesis, wherein the prosthesis comprises two prosthesis members which each is configured for attachment thereof to at least one of the bones at the joint, wherein one of the prosthesis members comprises a first attachment member which is configured for location in at least one of the bones at the joint and the other prosthesis member a second attachment member which is configured for location in at least one other bone at the joint, and wherein said one prosthesis member comprises a locking member and said other prosthesis member a lockable member.

The present invention also relates to a prosthesis for replacement of a joint, wherein the prosthesis comprises two prosthesis members which each is configured for attachment thereof to at least one of the bones at the joint, wherein one of the prosthesis members comprises a first screw-like attachment member which is configured for location in at least one of the bones at the joint and the other prosthesis member a second screw-like attachment member which is configured for location in at least one other bone at the joint, wherein said one prosthesis member comprises a socket member and said other prosthesis member a head member, wherein the socket member is configured with an attachment pin which is insertable into a hole in the first screw-like attachment member for location of the socket member therein, and wherein the head member is configured with an attachment pin which is insertable into a hole in the second screw-like attachment member for location of the head member therein.

BACKGROUND OF THE INVENTION

Prostheses of substantially the above-mentioned construction for artrodhesis already exist in many embodiments.

Examples of such embodiments are found in e.g. US 2010/0130978 A1. One of the drawbacks of this prior art construction is that it is adapted solely for artrodhesis (primary artrodhesis). Should there be a reason for replacing the prosthesis in order to again make the joint flexible, the entire prosthesis must be replaced. Furthermore, the prior art prosthesis does not include any member of the previously used prosthesis for making the joint flexible (artroplasty). Another drawback is the limited possibility to adjust the setting of the prosthesis members relative to each other and that adjustment must be performed by means of special tools.

Other similar constructions for artrodhesis of e.g. knee joints are found in DE 3347055 A1 and US 2009/0171463 A1.

In SE 528545 C2, a prosthesis for replacement of a joint (artroplasty) is described. This prior art prosthesis is configured substantially as defined above. This prior art construction however, is not adapted for artrodhesis and members thereof can not be used therefor.

SUMMARY OF THE INVENTION

Therefore, the object of the present invention is to provide a simple and yet extensively adjustable prosthesis for use at artrodhesis.

This object is arrived at, at the prosthesis for artrodhesis, by configuring the locking member with an attachment portion which is insertable into a hole in the first attachment member for location of the locking member therein, configuring the lockable member in one piece with the second attachment member and configuring the lockable member for adjustable setting thereof relative to the locking member and for fixation thereof, in set position, to the locking member.

This object is arrived at also by means of a prosthesis with, inter alia, a lockable member which alternatively is configured with an attachment portion which is insertable into a hole in the second attachment member for locating the lockable member therein.

Secondly, it is an advantage, should there be a need, that members of the prosthesis can be used to once again make the joint flexible (artroplasty).

The object of the present invention is also to configure members of a prosthesis for replacing a joint (artroplasty) such that these members can be used for making the joint rigid (artrodhesis).

This object is arrived at, at the prosthesis for artroplasty, by configuring the hole in the first screw-like attachment member at least partly to define a press fit with the attachment pin for the socket member and at least partly with a thread to permit, after removal of the socket member, during artrodhesis, tightening in the hole of a locking member which is configured to cooperate with a lockable member, which can be adjustably set relative to the locking member and fixed thereto in set position, of a second attachment member which replaces the second screw-like attachment member with the head member.

The above object is arrived at also by configuring the locking member to cooperate with a lockable member, which can be adjustably set relative to the locking member and fixed thereto in set position and which replaces the head member in the second screw-like attachment member.

BRIEF DESCRIPTION OF THE DRAWINGS

The invention will be further described in the following with reference to the accompanying drawings, in which.

DETAILED DESCRIPTION OF PREFERRED EMBODIMENTS

Figure 1:
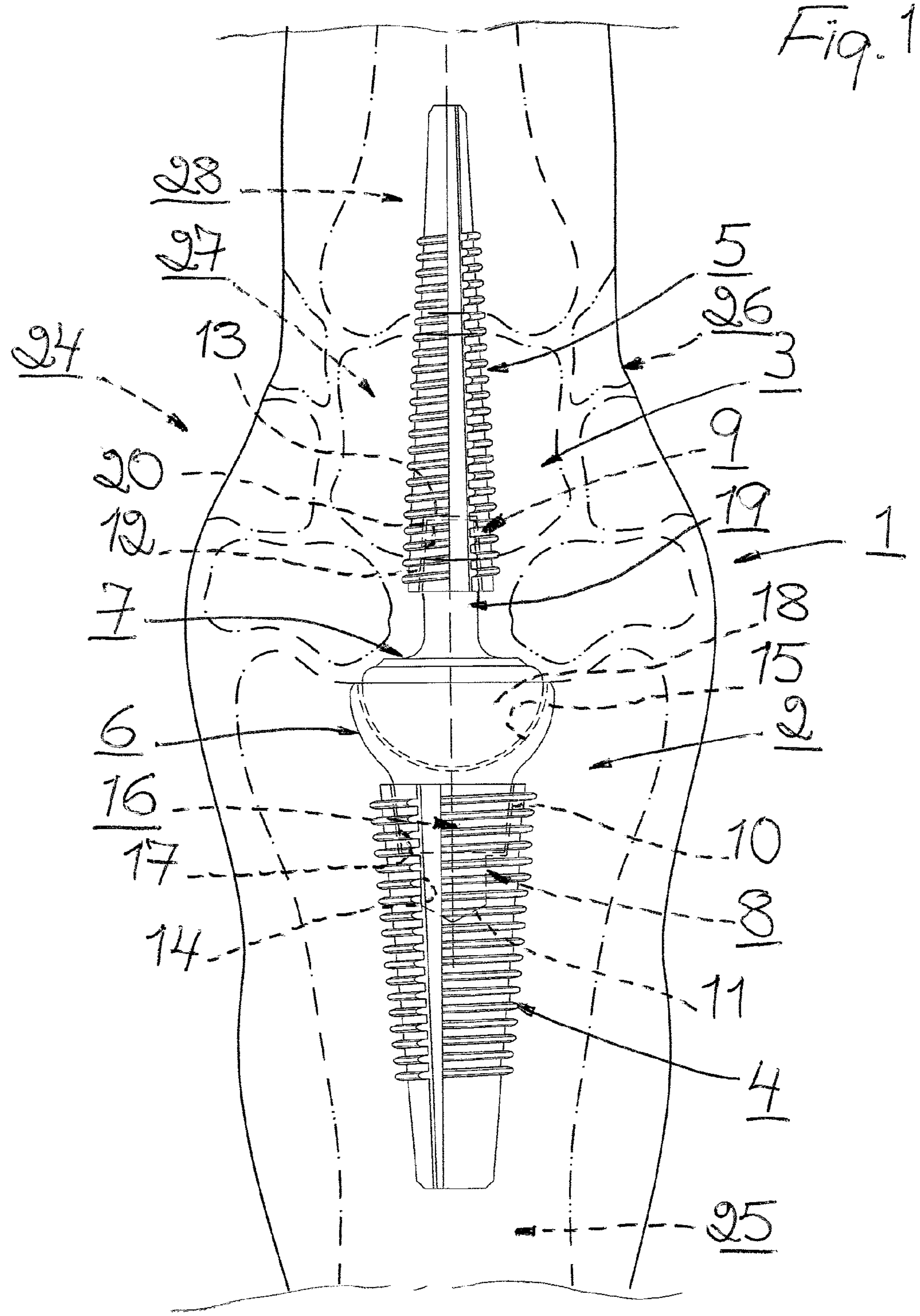
FIG. 1 is schematic side view of a prosthesis according to the invention for replacement of a joint (artroplasty), here a wrist, with screw-like attachment members of the prosthesis configured for artrodhesis of the wrist.

Thus, FIG. 1 illustrates a prosthesis according to the present invention for replacement of a wrist in order to preserve or maintain the flexibility of the wrist. This prosthesis is already described in SE 528545 C2, to which reference is made for further details. Therefore, the prosthesis will here be described in general terms only. The wrist prosthesis 1 comprises a first prosthesis member 2 and a second prosthesis member 3. The first prosthesis member 2 comprises a first screw-like attachment member 4 and the second prosthesis member 3 a second screw-like attachment member 5. The first prosthesis member 2 also comprises a socket member 6 and the second prosthesis member 3 a head member 7.

Each first and second screw-like attachment member 4, 5 is configured with a hole 8 and 9 respectively. The hole 8 in the first screw-like attachment member 4 extends in the form of a depression at a first end edge at which said attachment member has its largest diameter in an axial direction towards a second end edge of said attachment member at which the attachment member has its smallest diameter. The hole 9 in the second screw-like attachment member 5 extends as a depression at a first end edge at which said attachment member has its largest diameter in an axial direction towards a second end edge of said attachment member at which the attachment member has its smallest diameter.

The hole 8 in the first screw-like member 4 has its largest diameter at the first end edge and its side walls 10 have at least partly a conical shape, such that the hole tapers conically towards the bottom 11 of the hole. The hole 9 in the second screw-like member 5 has its largest diameter at the first end edge and its side walls 12 have at least partly a conical shape, such that the hole tapers conically towards the bottom 13 of the hole.

The hole 8 in the first screw-like member 4 is also at least in part provided with a thread 14.

The socket member 6 has a socket 15 defining a concave joint surface. An attachment pin 16 extends axially from the outer side of the socket 15. The attachment pin 16 has an axial outer side 17 which tapers conically towards its end edge. The shape and size of the attachment pin 16 and the shape and size of the hole 8 in the first screw-like attachment member 4 are chosen such that they, when pressed together in an axial direction, form a press fit, i.e. a connection which permits the socket member 6 and the first screw-like attachment member 4 to be brought to attach to each other when pressed together.

The head member 7 has a substantially spherical head 18 defining a convex joint surface of such shape that it fits into the joint surface of the socket 15 such that said joint surfaces can slide against each other and enable the flexibility of the joint. An attachment pin 19 extends axially from the outer side of the head 18. The attachment pin 19 has an axial outer side 20 which tapers conically towards its end edge. The shape and size of the attachment pin 19 and the shape and size of the hole 9 in the second screw-like attachment member 5 are chosen such that they, when pressed together in an axial direction, form a press fit, i.e. a connection which permits the head member 7 and the second screw-like attachment member 5 to be brought to attach to each other when pressed together.

The first and second screw-like attachment members 4, 5 are within the holes 8, 9 configured with additional holes (not shown) to permit a screw pin 21 of a screw tool 22, e.g. a screw driver, to be inserted into the holes for tightening or securing by screwing the screw-like attachment members in the respective bone. The holes for the screw tool 22 are not round, e.g. multi-edge holes such as hexagonal holes or similar.

Each first and second screw-like attachment member 4, 5 is at the illustrated embodiment tapering conically from the first end edge in a direction towards the second end edge. The conical shape can extend the entire distance between said end edges, but this is not a requirement. Each first and second screw-like attachment member 4, 5 is also configured with external threads for tightening of the attachment members in the respective bone. The external threads may have self-tapping properties and extend in different degrees along the screw-like attachment members 4, 5.

Each first and second screw-like attachment member 4, 5 may be configured with an axial through-hole (not shown) such that the attachment member can be threaded onto a guide wire 23 which is adapted for arrangement at the respective bone and which is adapted to guide the attachment members when these members are screwed into the respective bone.

The illustrated prosthesis may, as stated above, be provided at a wrist 24 for replacement thereof and at the same time maintain most of the flexibility in said wrist (artroplasty). The bones in such a wrist and bones in the hand and arm are shown schematically in FIG. 1 with broken lines and these bones may be the radius 25, one or more bones in carpus 26, e.g. the capitate 27, and a metacarpal bone 28, e.g.

the third metacarpal bone. As is apparent in FIG. 1, the first screw-like attachment member 4 is screwed into the radius 25 and is therefore configured thicker and shorter than the second screw-like attachment member and it has a larger hole 8 than the hole 9 in the second attachment member. The second screw-like attachment member 5 is at the illustrated wrist 24 screwed into the capitate 27 and the metacarpal bone 28.

FIGS. 2-6 illustrate how the first and second screw-like attachment members 4, 5 can be provided in the respective bone 25, 27 and 28.

Figure 2:
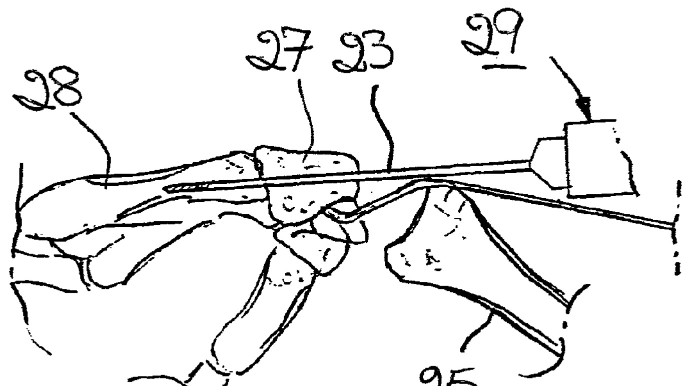
FIGS. 2-6 are schematic side views of different moments during location of the screw-like attachment members forming parts of the prosthesis according to FIG. 1.

As shown in FIG. 2, a guide wire 23 which is attached to a drilling machine 29, is drilled through the capitate 27 and into the metacarpal bone 28. Then, the drilling machine 29 is removed, while the guide wire 23 is left in position.

Figure 3:
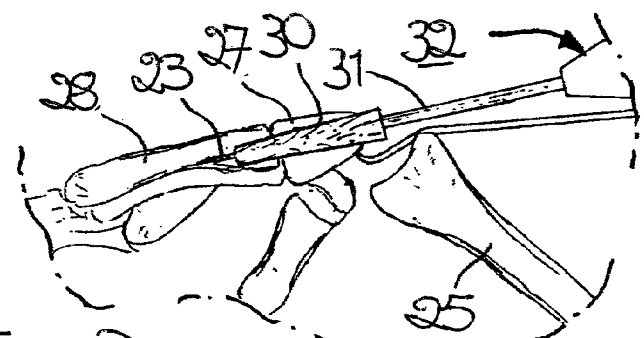

As illustrated in FIG. 3, a conical drill 30 and a tubular bracket 31 by means of which the drill 30 is mounted on a drilling machine 32, are then threaded onto the guide wire 23 and conical holes are drilled in the capitate 27 and the metacarpal bone 28.

Figure 4:
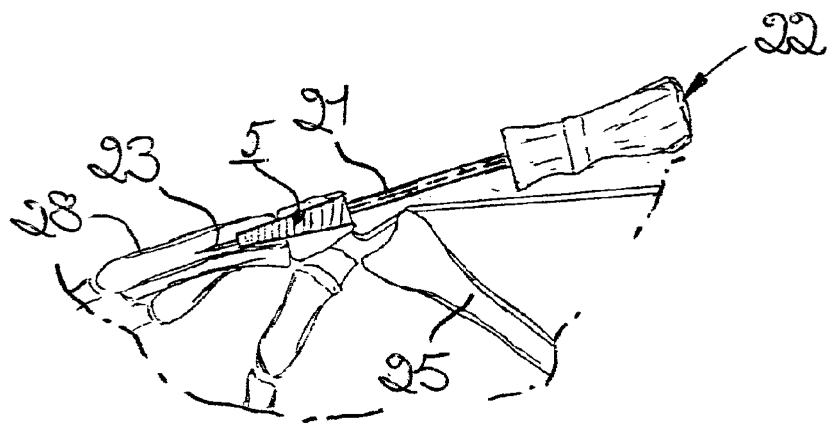

As illustrated in FIG. 4, the second screw-like attachment member 5 is then threaded onto the guide wire 23. Thereafter, the cannulated screw pin 21 of the screw driver 22 is threaded onto the guide wire 23 and into the hole for the screw driver in the second screw-like attachment member 5, the screw driver is rotated for tightening or securing by screwing said attachment member in the holes in the capitate 27 and the metacarpal bone 28. Finally, the screw driver 22 and the guide wire 23 are removed.

Figure 5:
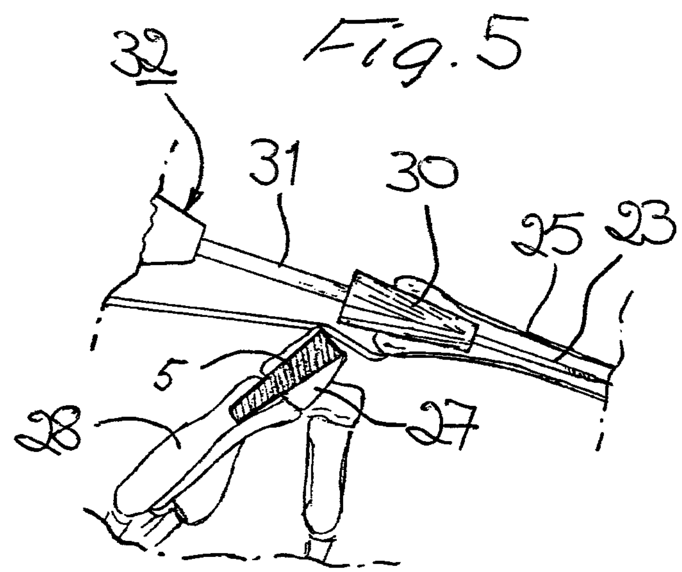
Figure 6:
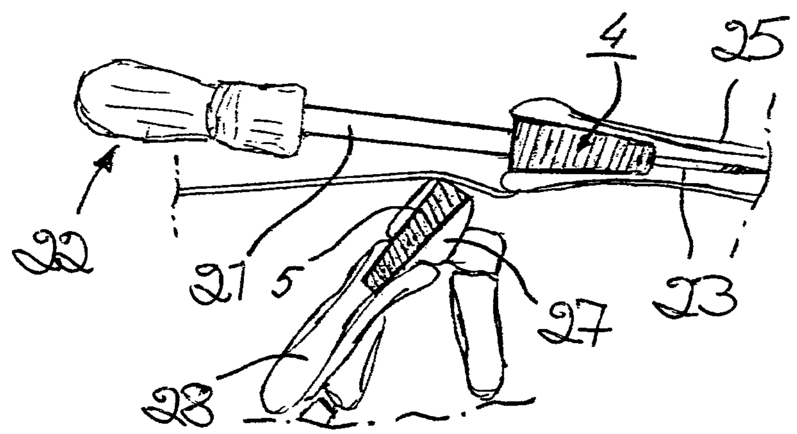
Figure 7:
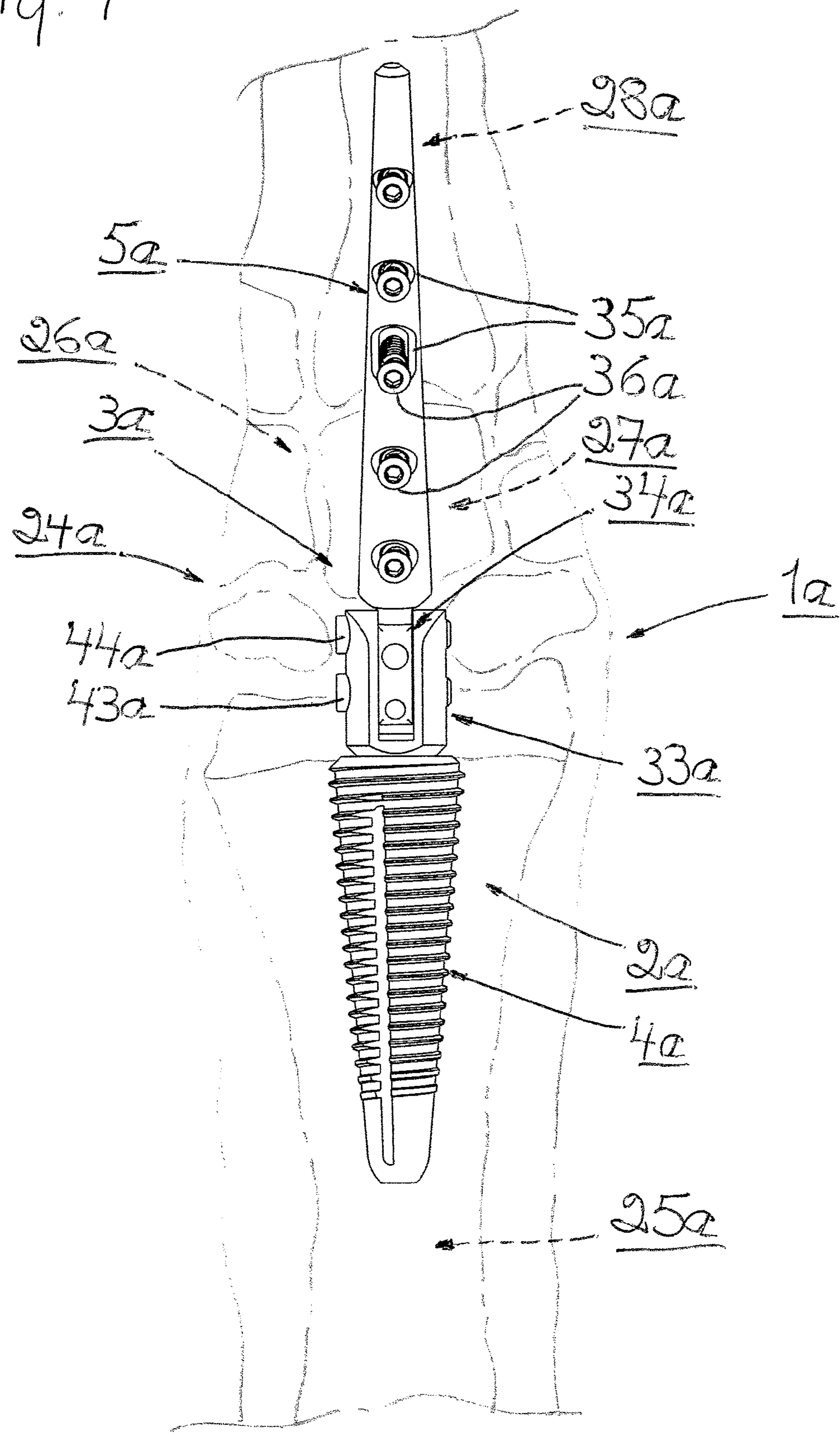
FIG. 7 is a schematic side view of a first embodiment of a prosthesis according to the invention for artrodhesis of a wrist.
Figure 8:
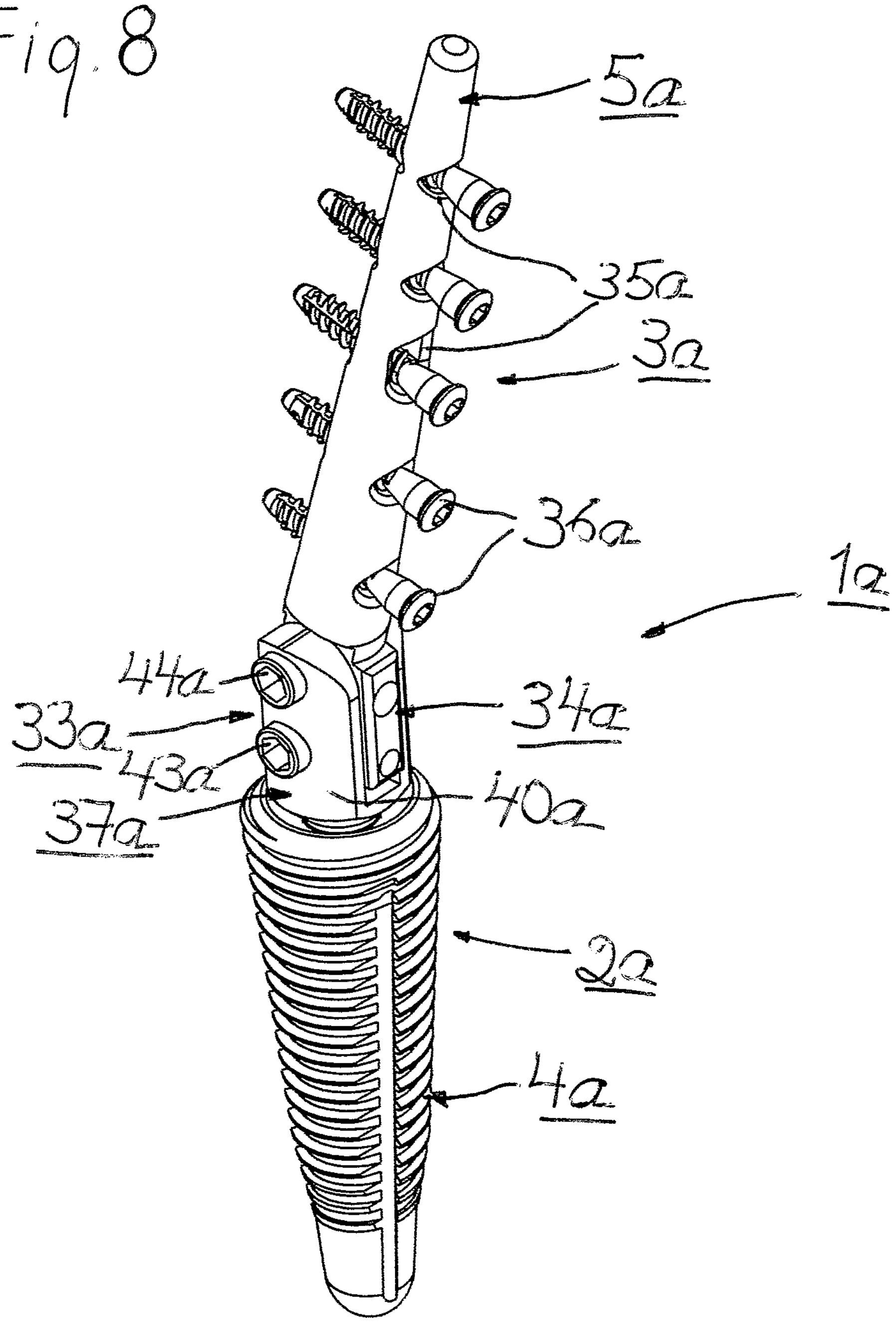
FIG. 8 is a schematic perspective view of the prosthesis of FIG. 7.
Figures 9, 10:
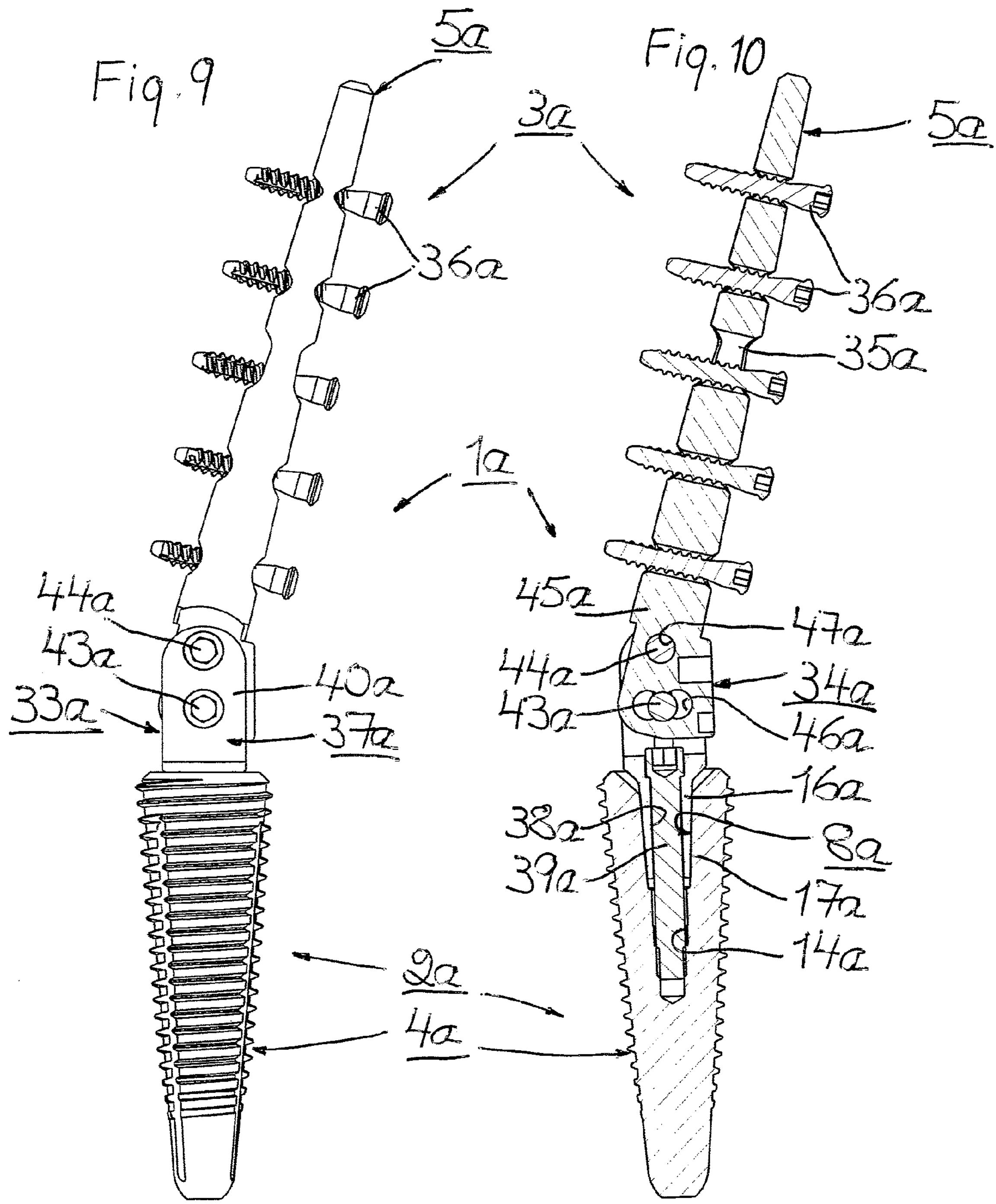
FIG. 9 is an additional schematic side view of the prosthesis according to FIGS. 7 and 8.
FIG. 10 is schematic sectional view of the prosthesis according to FIG. 9.

As is apparent from FIGS. 5 and 6, the same procedure is used for providing the first screw-like attachment member 4 in the radius 25. Thus, it is apparent from FIG. 5 that a guide wire 23 is fixedly attached to the radius 25, that a conical drill 30 (which is larger than the drill 30 in FIG. 3) is threaded onto the guide wire and that one has drilled a conical hole in the radius by means of said drill. In FIG. 6, it is shown that one has tightened or secured by screwing the first screw-like attachment member 4 in the radius 25 by means of the screw driver 22 and has then removed the guide wire 23 from the radius.

The first and second screw-like attachment members 4, 5 may consist of at least one material, while the socket and head members 6, 7 may consist of at least one other material. Thus, each first and second screw-like attachment member 4, 5 may comprise a core of a metal and an outer layer of a material which can be dissolved when said attachment members are implanted.

Said core may consist of a titanium alloy and the dissolvable material may consist of or include calcium phosphate.

The socket and head members 6, 7 may consist of a chromium-cobalt-alloy.

Figures 12, 13:
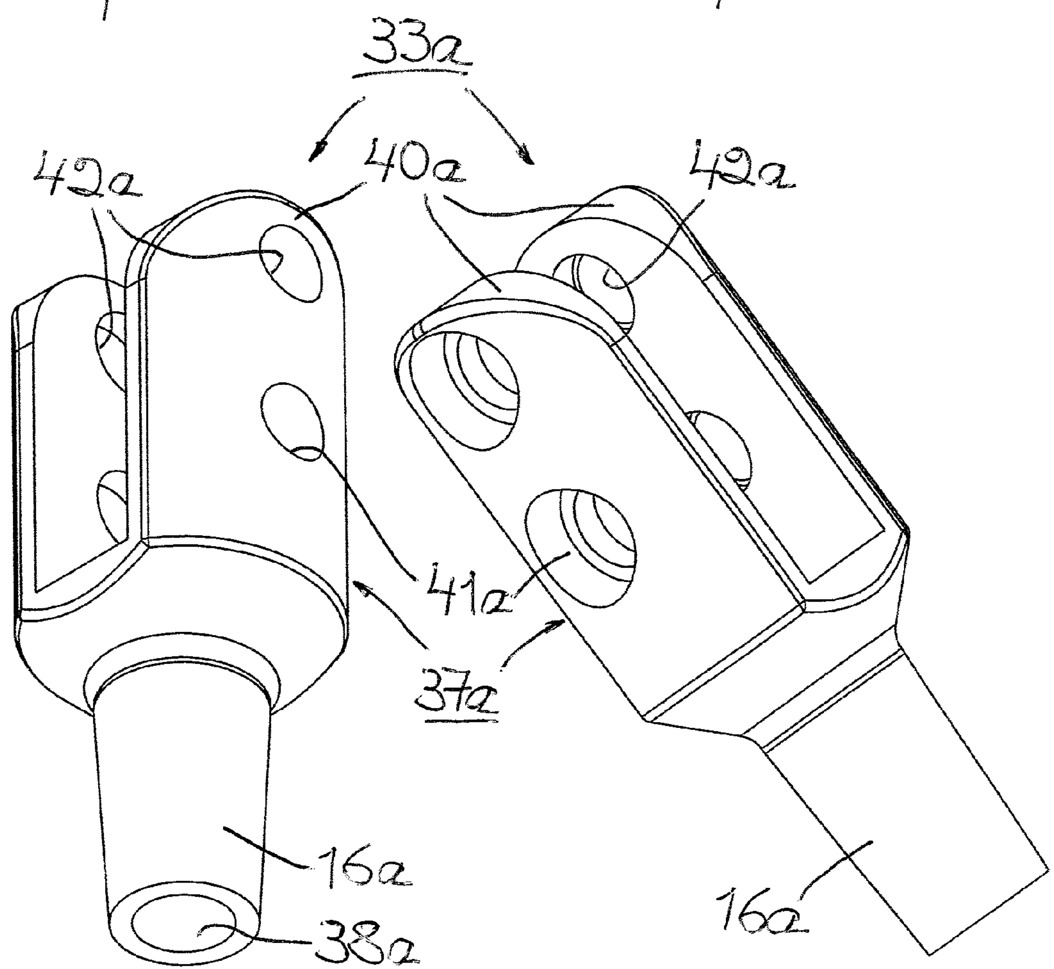
FIGS. 12 and 13 are enlarged schematic perspective views of the locking member of FIG. 11.
Figure 14:
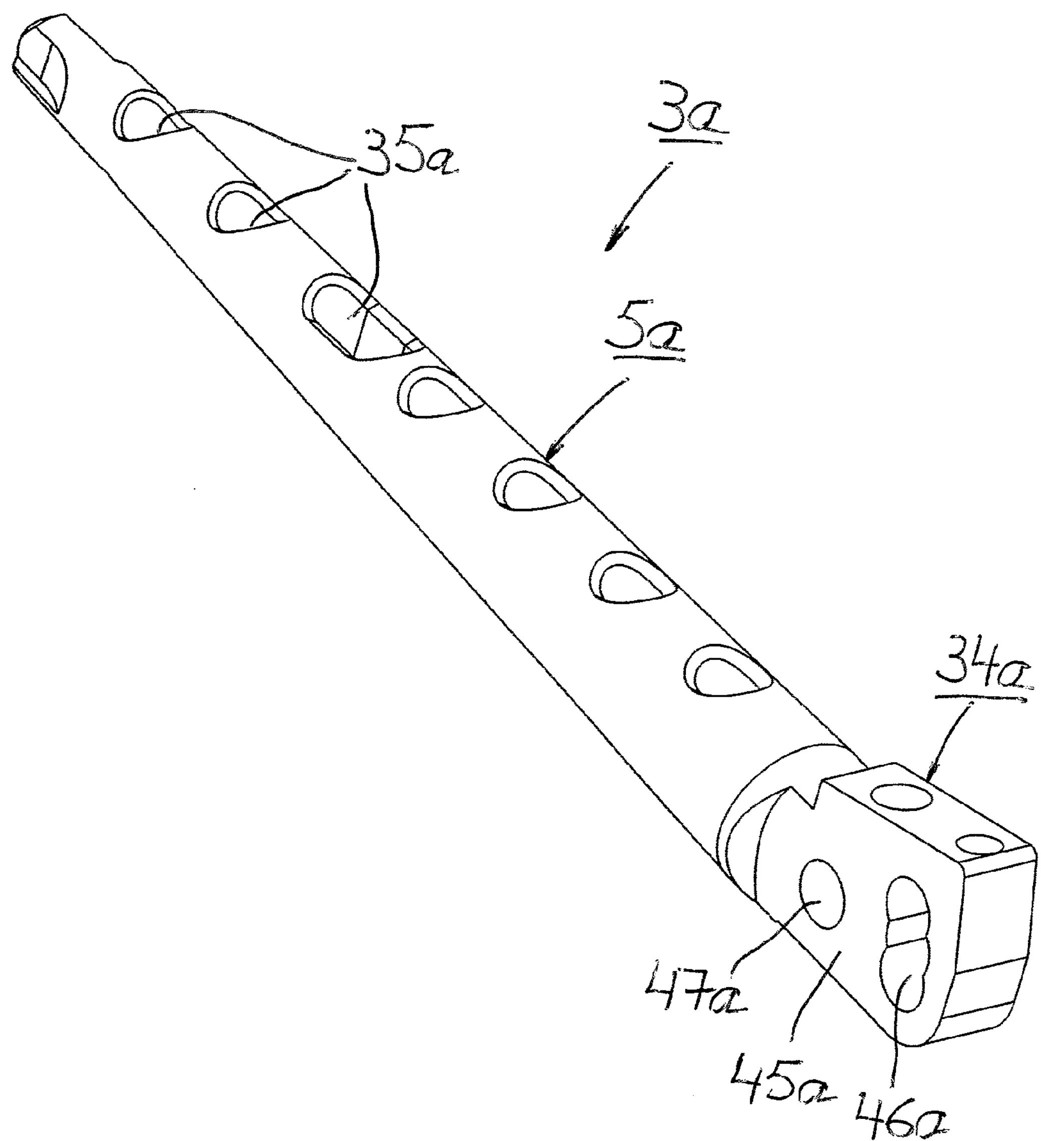
FIG. 14 is an enlarged schematic perspective view of a somewhat modified attachment member forming part of the prosthesis according to FIGS. 7-10 and with an integrated lockable member.
Figure 16:
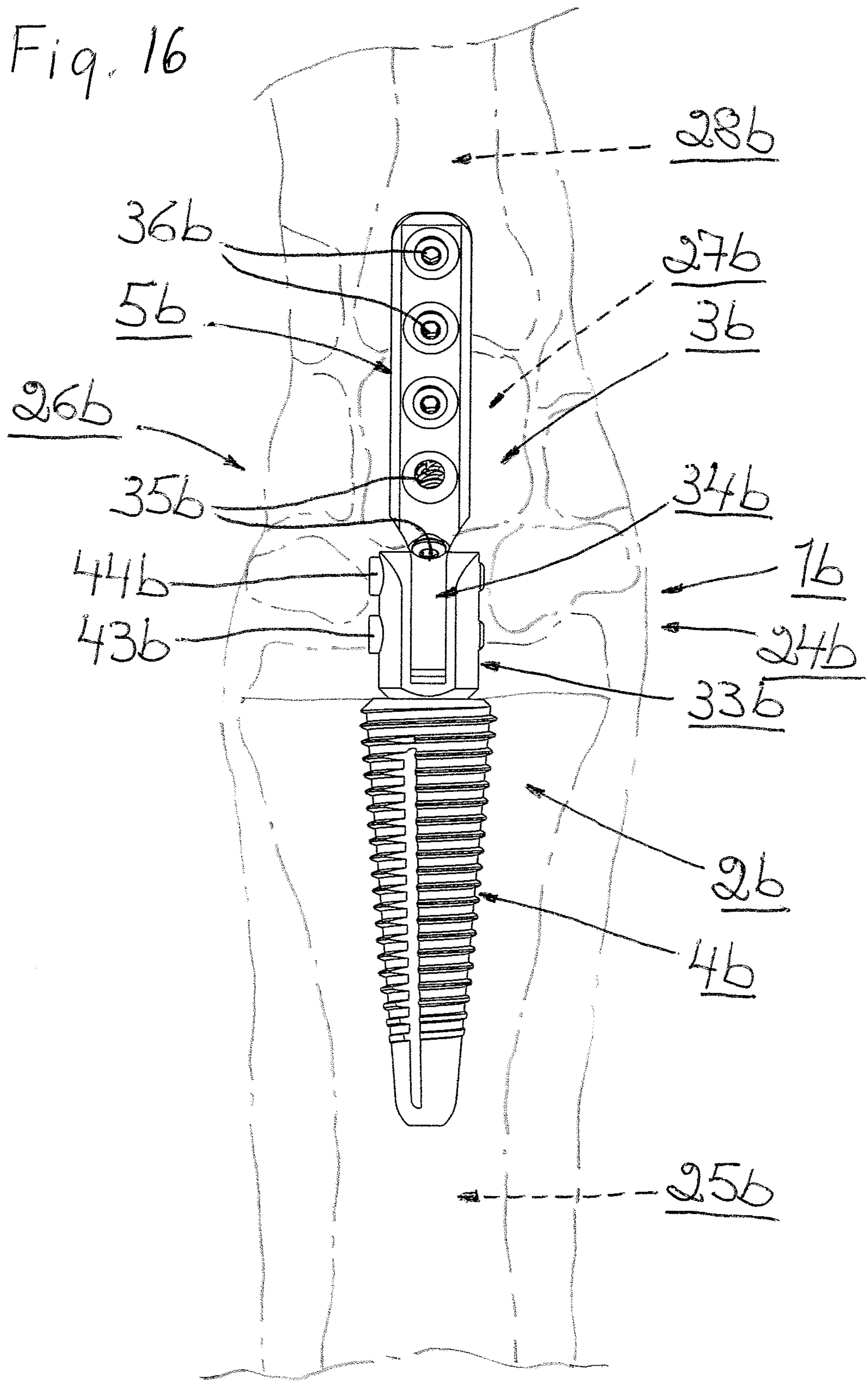
FIG. 16 is a schematic side view of a second embodiment of a prosthesis according to the invention for artrodhesis of a wrist.
Figures 17, 18:
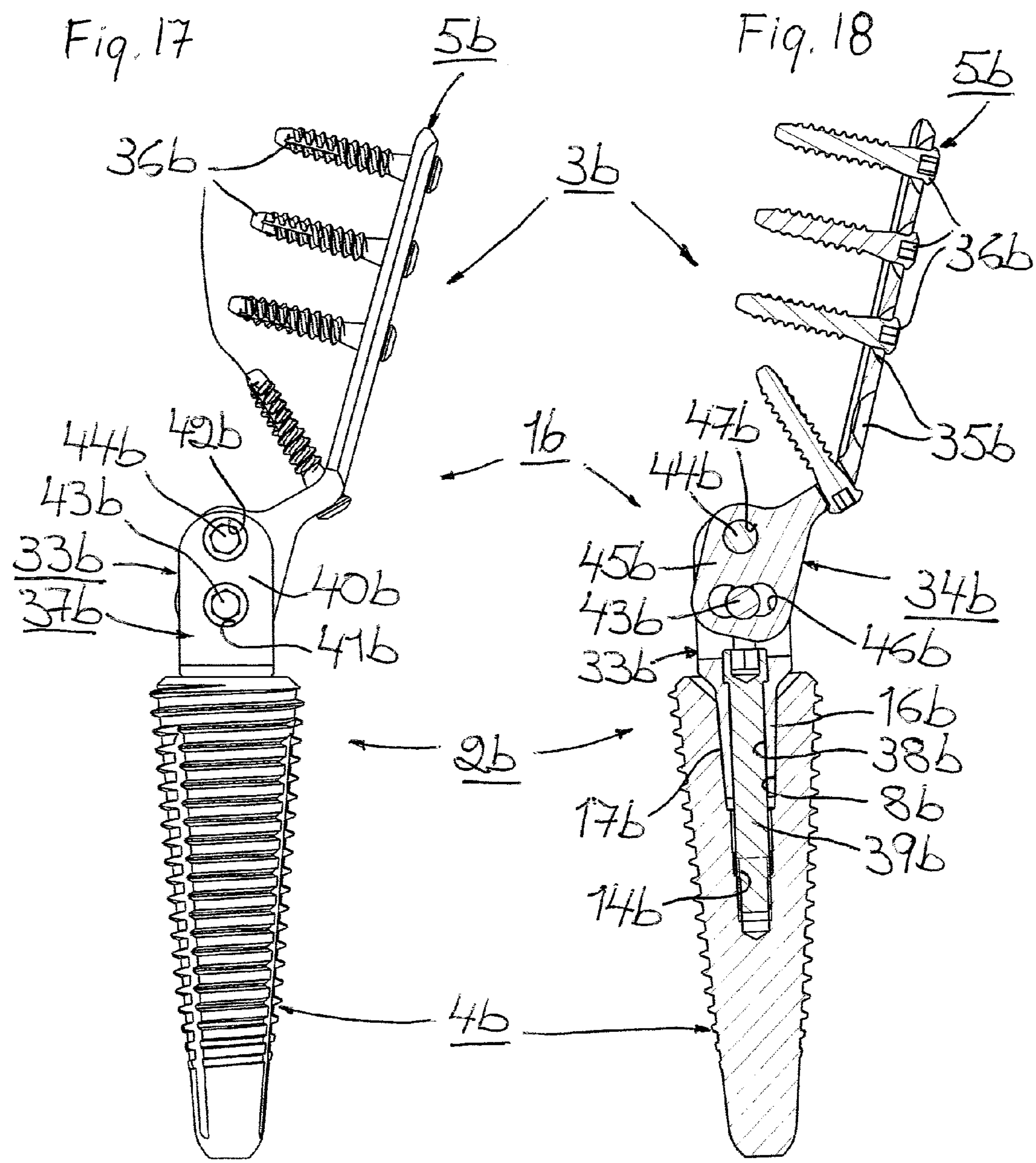
FIG. 17 is an additional schematic side view of the prosthesis according to FIG. 16.
FIG. 18 is schematic sectional view of the prosthesis according to FIG. 17.
Figure 19:
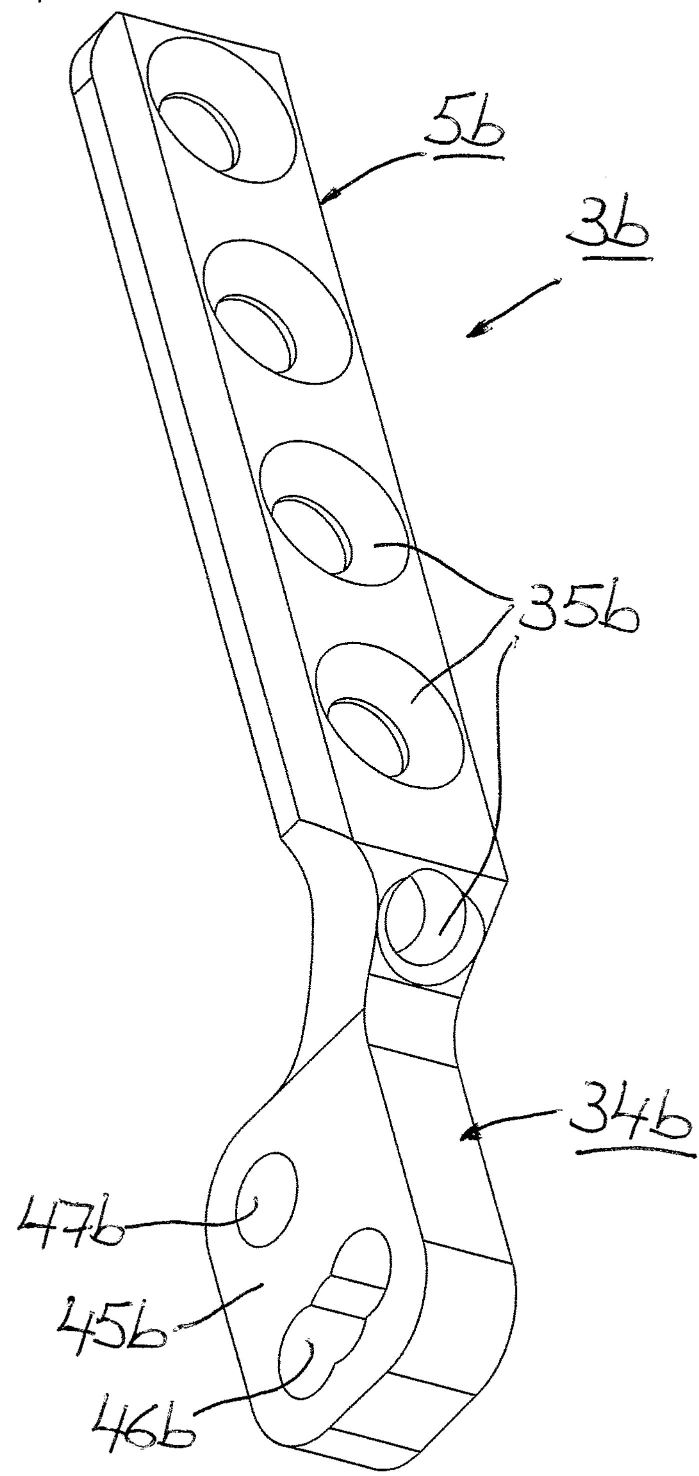
FIG. 19 is an enlarged schematic perspective view of an attachment member forming part of the prosthesis according to FIGS. 16-18 and with an integrated lockable member.
Figure 20:
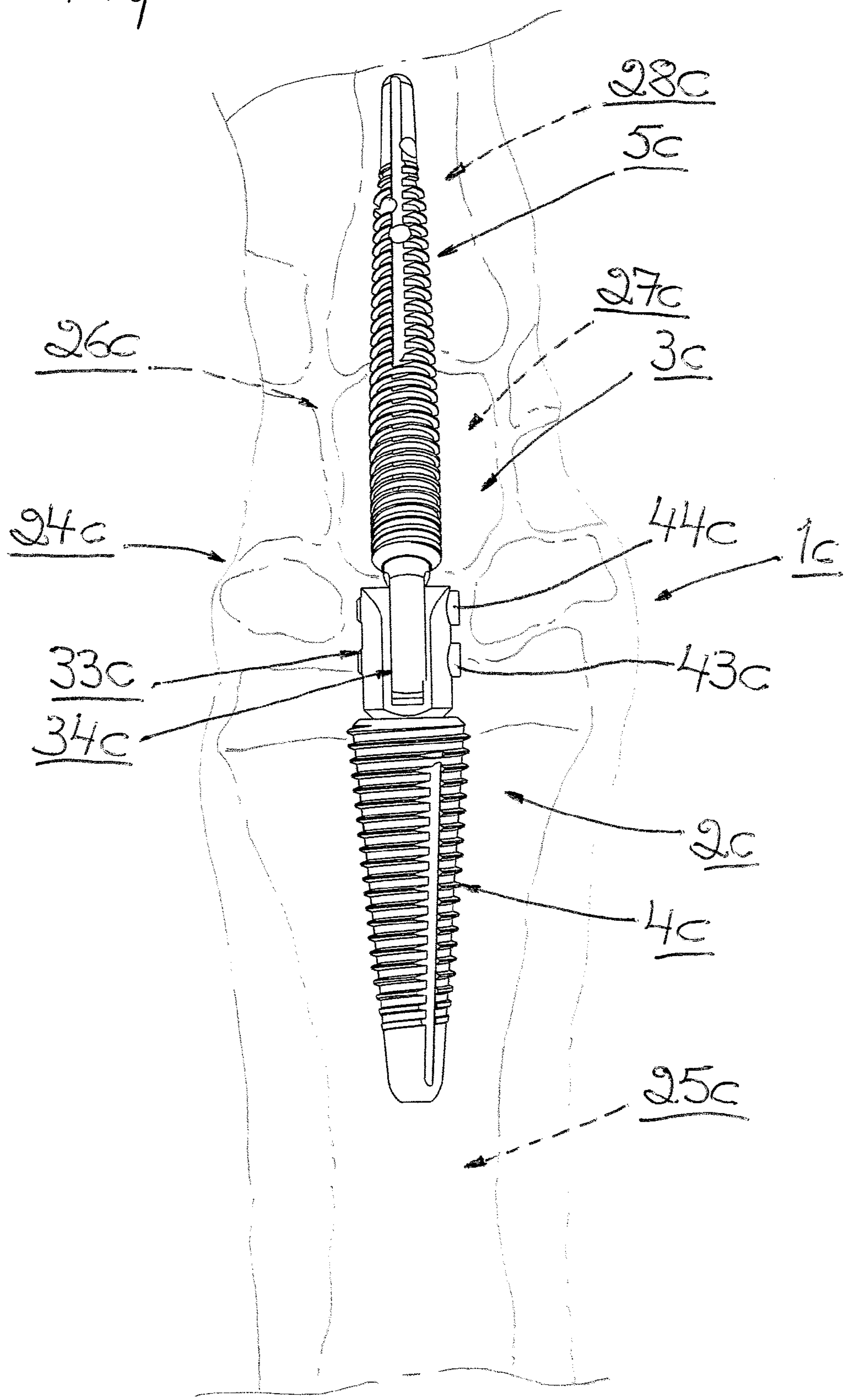
FIG. 20 is a schematic side view of a third embodiment of a prosthesis according to the invention for artrodhesis of a wrist.
Figure 21:
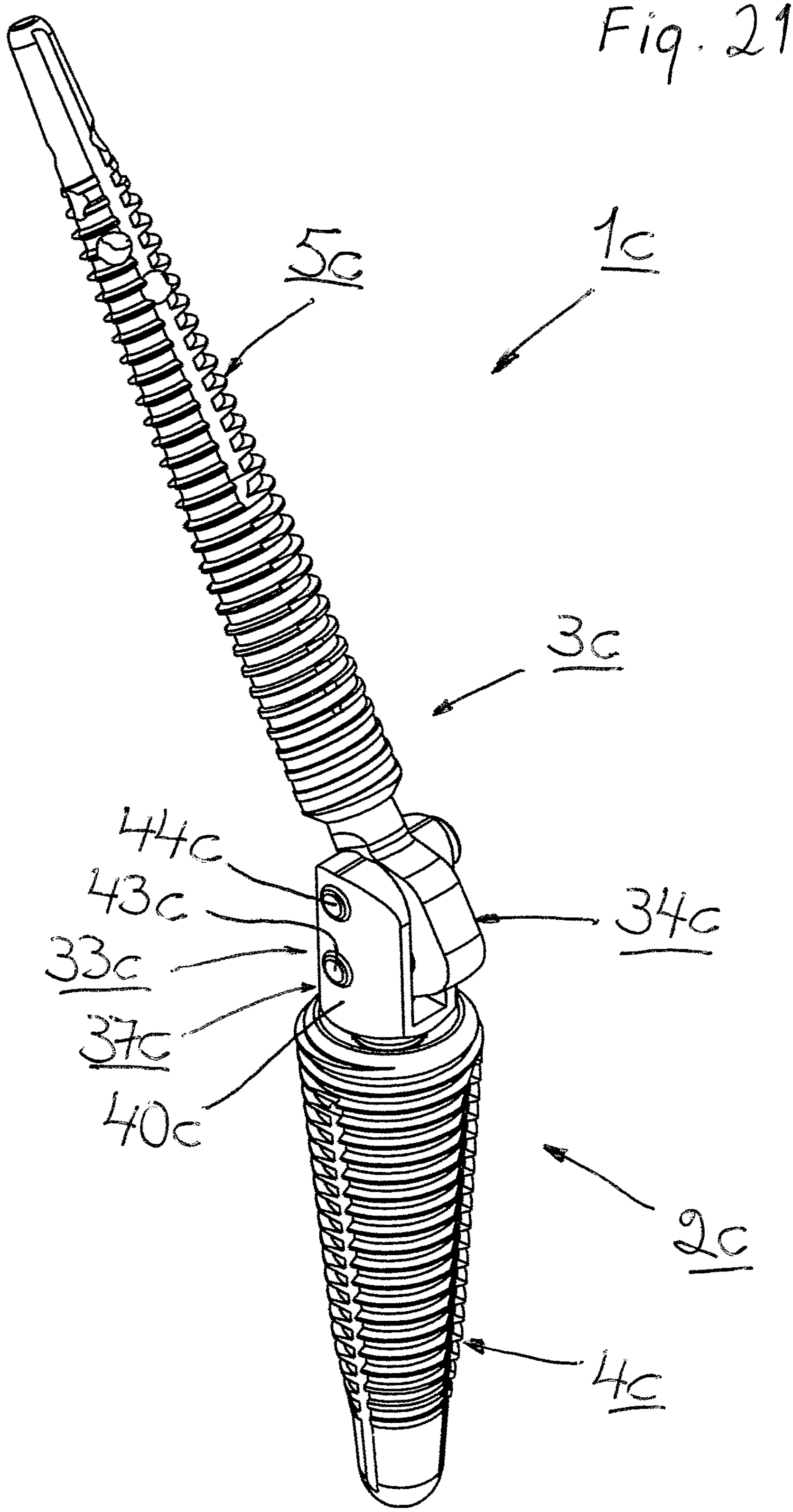
FIG. 21 is a schematic perspective view of the prosthesis of FIG. 20.
Figures 22, 23:
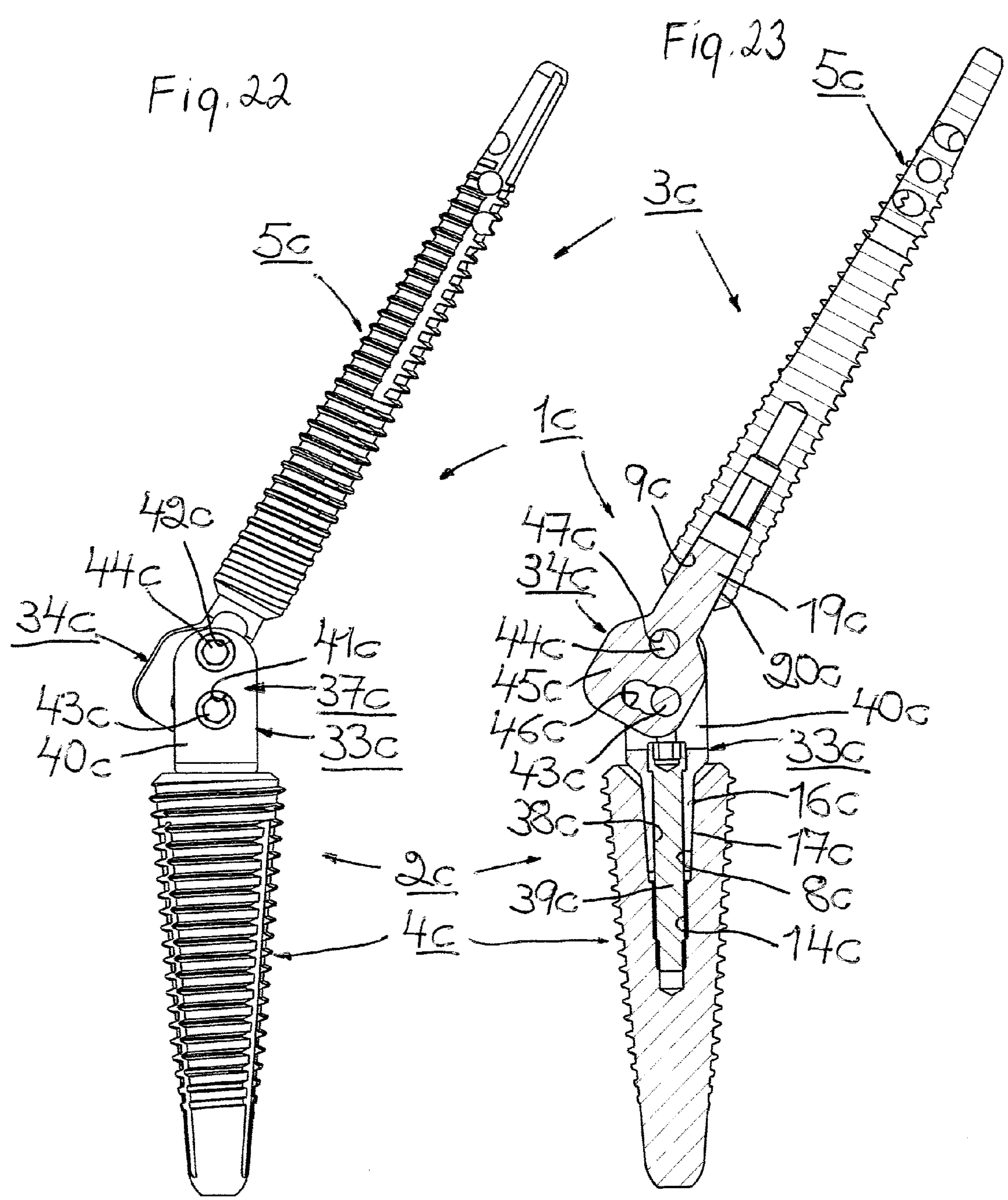
FIG. 22 is an additional schematic side view of the prosthesis according to FIGS. 20 and 21.
FIG. 23 is schematic sectional view of the prosthesis according to FIG. 22.

The prosthesis 1 described above is, as mentioned, adapted for replacing a wrist for maintaining its flexibility. However, the first screw-like attachment member 4 of the prosthesis 1 may when required be used also for artrodhesis. To this end, the hole 8 in the first screw-like attachment member 4 is at least in part configured to define a press fit with the attachment pin 16 for the socket member 6 and is at least partly threaded (thread 14) to permit tightening in the hole of a locking member (33*a; 33b*, see preferably FIGS. 12 and 13 showing the locking member 33*a*) after removal of said socket member, said locking member being configured to cooperate with a lockable member (34*a;* 34*b*, see FIG. 13 and, alternatively, FIG. 17) of a second attachment member (5*a;* 5*b*, see FIG. 14; 19) replacing the second screw-like attachment member 5 with the head member 7, said lockable member being configured to be adjustably set relative to the locking member and fixed thereto in set position. The prosthesis 1 will hereby be configured substantially as the prosthesis 1*a* according to FIGS. 7-10 or as the prosthesis 1*b* according to FIGS. 16-18.

Figure 24:
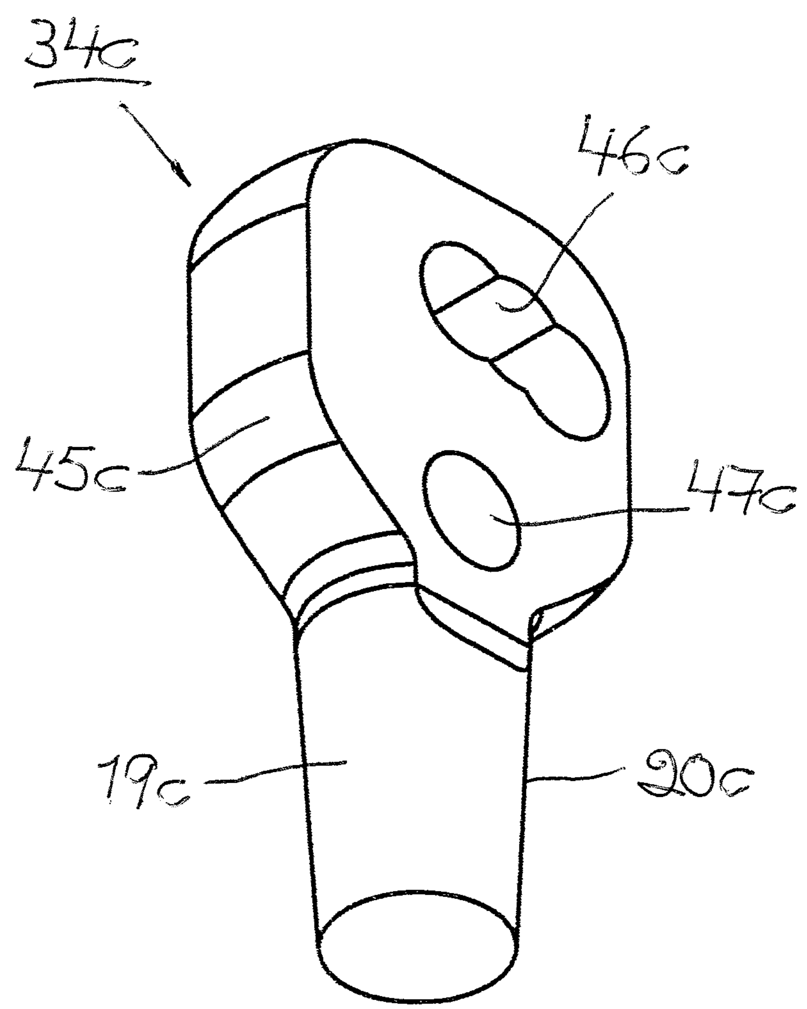
FIG. 24 is an enlarged schematic perspective view of the lockable member of the prosthesis of FIGS. 20-23.
Figure 25:
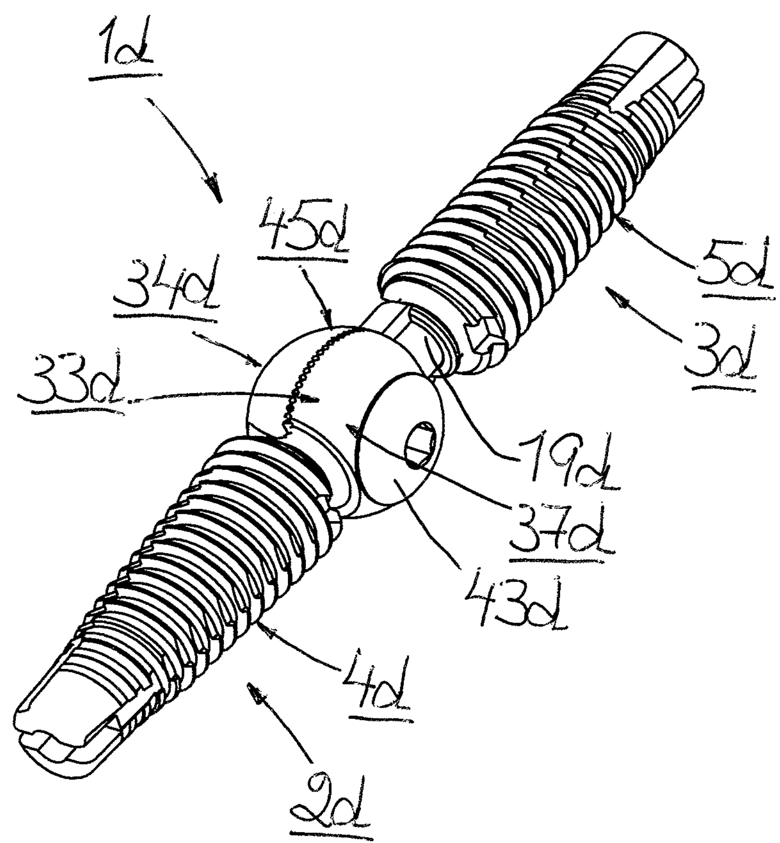
FIG. 25 is a schematic perspective view of a fourth embodiment of a prosthesis according to the invention for artrodhesis of a wrist.
Figure 28:
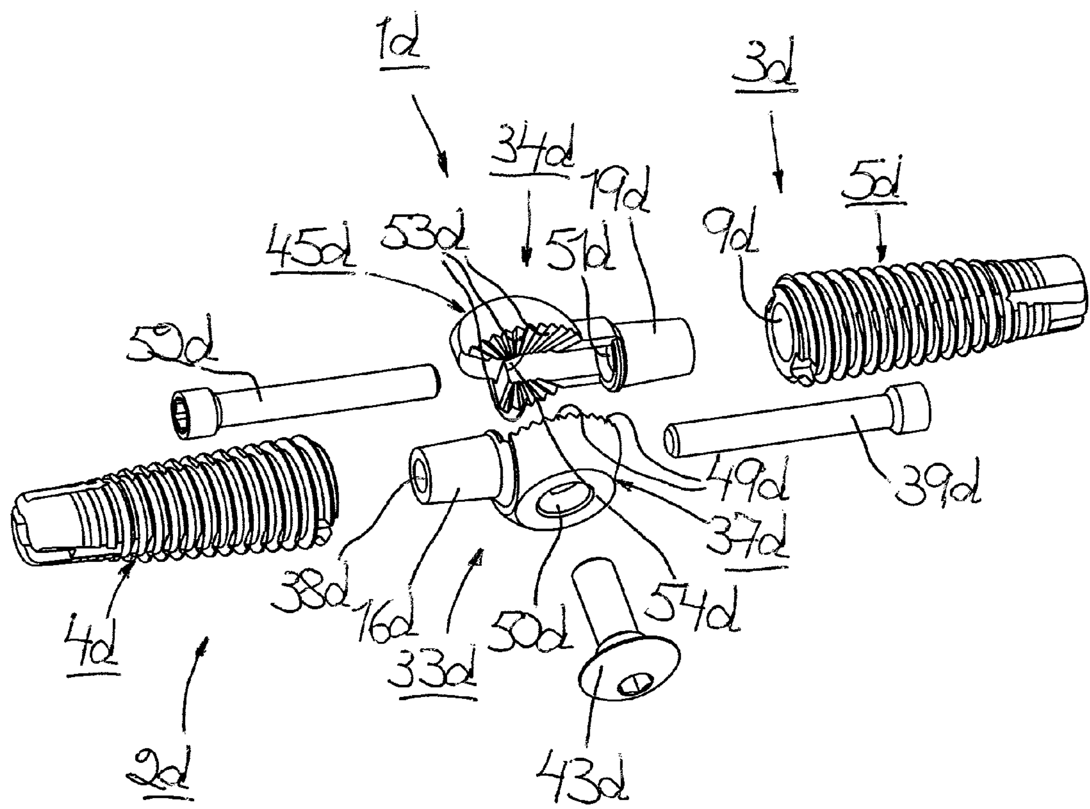
FIG. 28 is an exploded view of the prosthesis according to FIGS. 25-27.

Alternatively, if the second screw-like attachment member 5 is undamaged and has not loosened from the surrounding bone tissue, the locking member (33*c*, with the same configuration as the locking member 33*a* according to FIGS. 12 and 13; 33*d*) is configured to cooperate with a lockable member (34*c*, see FIG. 24; 34*d*, see FIG. 28) which replaces the head member 7 in the second screw-like attachment member 5, and which is configured to be adjustably set relative to the locking member and fixed thereto in set position. The prosthesis 1 will hereby be configured substantially as the prosthesis 1*c* according to FIGS. 20-23 or as the prosthesis 1*d* according to FIGS. 25-28.

Figures 26, 27:
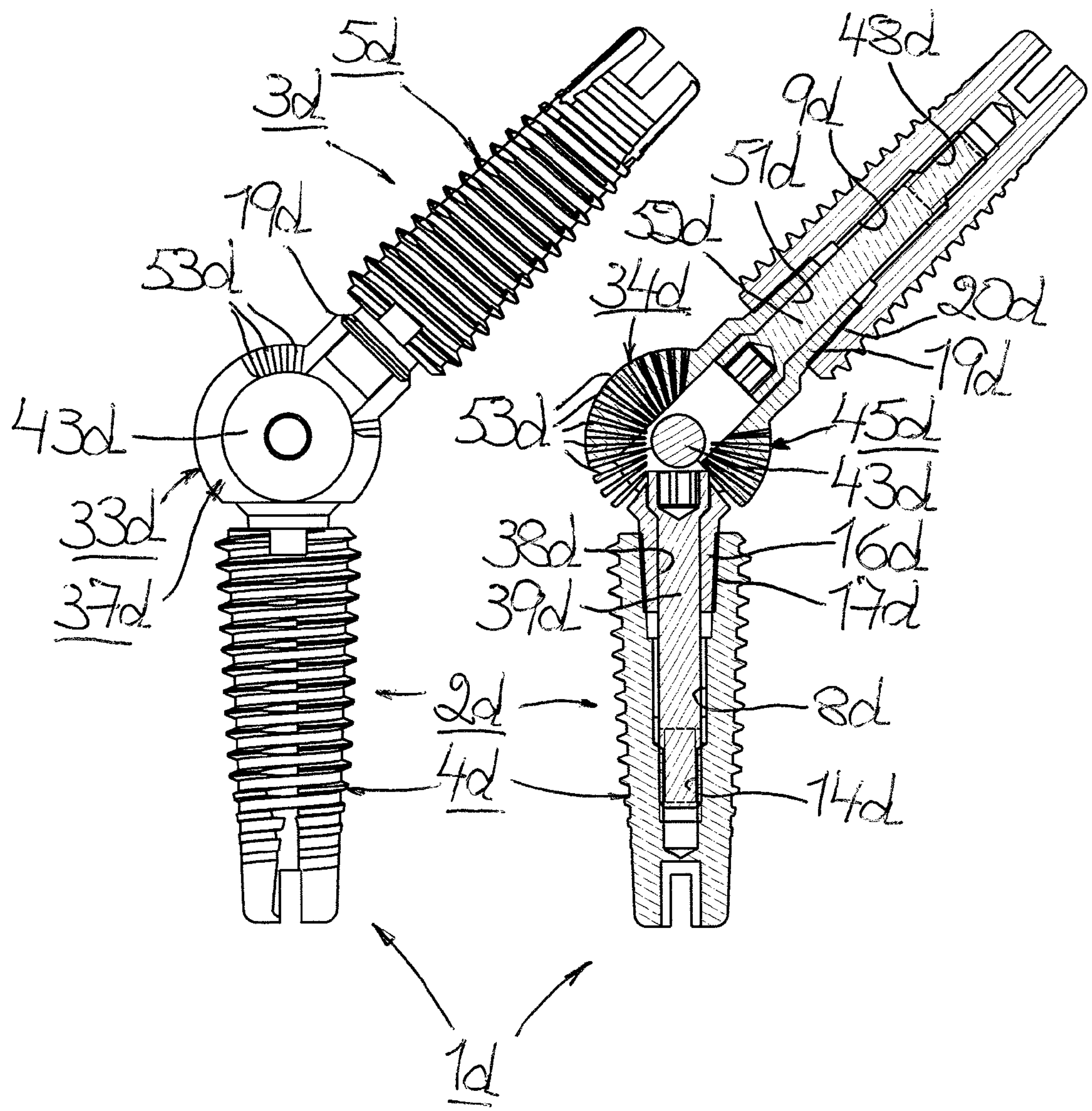
FIG. 26 is a schematic side view of the prosthesis according to FIG. 25.
FIG. 27 is schematic sectional view of the prosthesis according to FIG. 26.

The hole 9 in the second screw-like attachment member will then be configured to define a press fit also with the lockable member (34*c*, see FIG. 24), alternatively also configured with a thread for tightening or securing by screwing in the lockable member (34*d*, see FIG. 27).

At a primary artrodhesis, i.e. when a decision has been taken that an artrodhesis of in this case a wrist must be performed immediately, the prosthesis is of course in principal constructed in a corresponding way as the prosthesis 1 described above.

Thus, the prosthesis 1*a* of FIGS. 7-15 for a wrist 24*a* comprises, as previously, a first prosthesis member 2*a* and a second prosthesis member 3*a*. The first prosthesis member 2*a* comprises a first attachment member 4*a* and the second prosthesis member 3*a* second attachment member 5*a*. The first prosthesis member 2*a* also comprises a locking member 33*a* instead of a socket member 6 and the second prosthesis member 3 a lockable member 34*a* instead of a head member 7.

The first attachment member 4*a* is in the illustrated embodiment configured as a screw, but can also have another shape.

The second attachment member 5*a* is in the embodiment of FIGS. 7-15 made in one piece, i.e. integral with the lockable member 34*a*. The second attachment member 5*a* comprises thereby an elongated, from the lockable member 34*a* substantially conically tapering member with transversely through said member and substantially in line in the longitudinal direction thereof configured holes 35*a* for means 36*a* for fixation or attachment of said second attachment member in the capitate 27*a* and the metacarpal bone 28*a*. In the illustrated embodiment, the second attachment member 5*a* has five (or seven, FIG. 14) holes 35*a* for attachment means 36*a*. At least one of the holes 35*a* is a long-hole for reasons described below and said attachment means 36*a* consist of so called cortical screws.

The first attachment member 4*a* is configured with a hole 8*a*. This hole 8*a* has in turn at least partly a conical shape and is at least partly configured with a thread 14*a*, as is the hole 8.

The locking member 33*a* is configured with an attachment portion 16*a*, e.g. an attachment pin, which is insertable into the hole 8*a* in said first attachment member 4*a* for location of the locking member therein. Accordingly, the attachment portion 16*a* has a conically tapering outer side 17*a*. The shape and size of the attachment portion 16*a* and the shape and size of the hole 8*a* in the first attachment member 4*a* are chosen such that they, when pressed together in an axial direction, form a press fit, such that the locking member 33*a* and the first attachment member 4*a* can be brought to attach to each other by pressing said members together.

The lockable member 34*a* is adjustably settable relative to the locking member 33*a* and in set position fixable to the locking member.

Except for the attachment portion 16*a*, the locking member 33*a* is also configured with a locking portion 37*a* which is connected to the attachment portion. The locking portion 37*a* is configured for fixation or attachment of the lockable member 34*a* thereto. The attachment portion 16*a* is configured with a hole 38*a* which extends through said attachment portion and in the longitudinal direction thereof for insertion therein of a partly threaded attachment means 39*a* for tightening or securing by screwing the locking member 33*a* to the first attachment member 4*a* by bringing said attachment means to cooperate with the threaded portion 14*a* of the hole 8*a* in said first attachment member. The locking portion 37*a* of the locking member 33*a* is in the illustrated embodiment substantially U-shaped and comprises two shanks 40*a* with holes 41*a*, 42*a* provided in said shanks opposite each other. Each shank 40*a* is in the illustrated embodiment configured with two holes 41*a*, 42*a* which extend through the shank and substantially in line in the longitudinal direction of the locking portion 37*a*. One hole 41*a* is configured for a locking means 43*a* (inclination screw) for fixation or attachment of the lockable member 34*a* to the locking member 33*a* and the other hole 42*a* is configured for an axis 44*a* about which the lockable member can pivot for adjustable setting thereof relative to the locking member.

Correspondingly, the lockable member 34*a* comprises in the illustrated embodiment a substantially flange-like lockable portion 45*a* for insertion between the shanks 40*a* of the locking portion 37*a* of the locking member 33*a*. The flange-like lockable portion 45*a* is configured with a curved long-hole 46*a*, which extends transversely therethrough, for said locking means 43*a* and with a hole 47*a*, also extending transversely through said lockable portion, for the axis 44*a* about which the lockable member can pivot for adjustable setting thereof relative to the locking member. At insertion of the flange-like lockable portion 45*a* between the shanks 40*a* of the locking portion 37*a* of the locking member 33*a*, portions of the long-hole 46*a* are brought in line with the holes 41*a* for the locking means 43*a* in said shanks for fixation or attachment of the lockable portion to the locking portion of the locking member and the hole 47*a* for the pivoting axis 44*a* is brought in line with the holes 42*a* for said pivoting axis in said shanks. The lockable portion 45*a* of the lockable member 34*a* may have another shape than the flange-like shape as long as it fulfils its function and permits insertion thereof between the shanks 40*a* of the locking portion 37*a* of the locking member 33*a*. The long-hole 46*a* in the lockable portion 45*a* of the lockable member 34*a* is configured with a plurality of, e.g. three fixed positions (see e.g. FIGS. 10 and 14) corresponding with different angular positions of the lockable member relative to the locking member.

Figure 11:
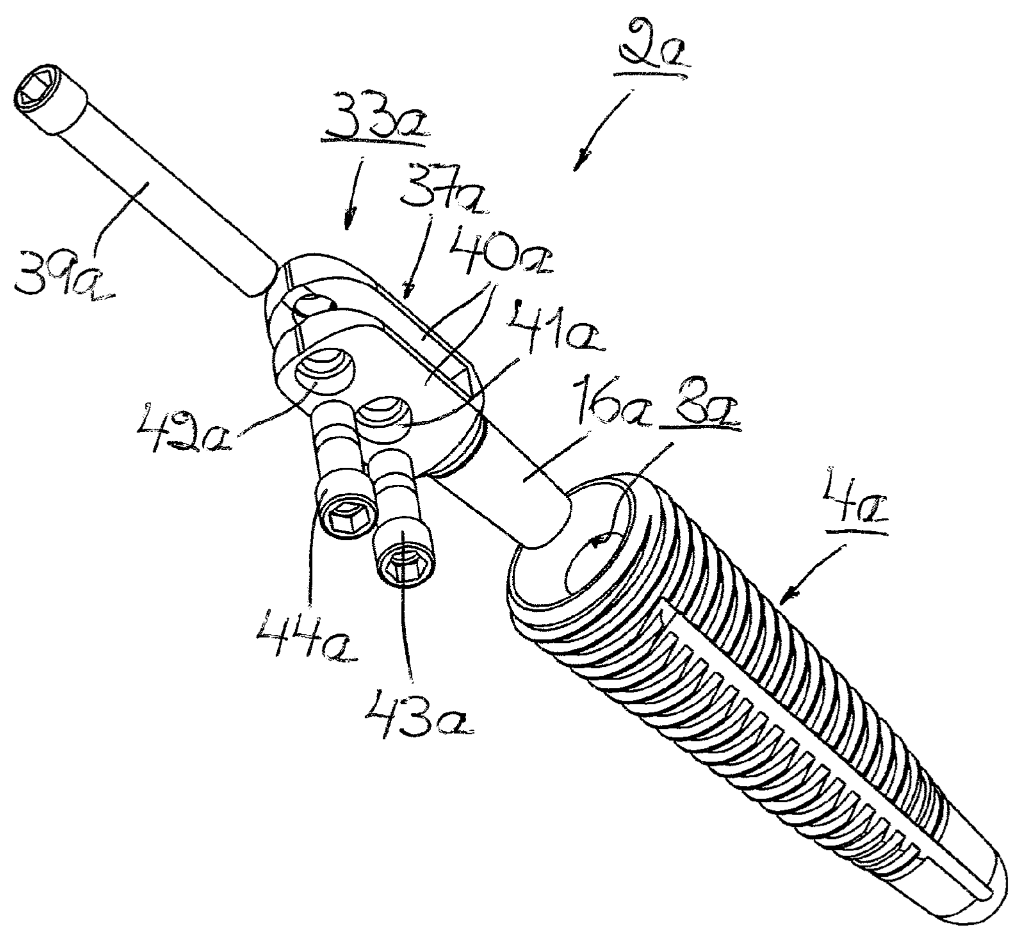
FIG. 11 is a schematic perspective view of an attachment member forming part of the prosthesis and with a locking member positionable therein.
Figure 15:
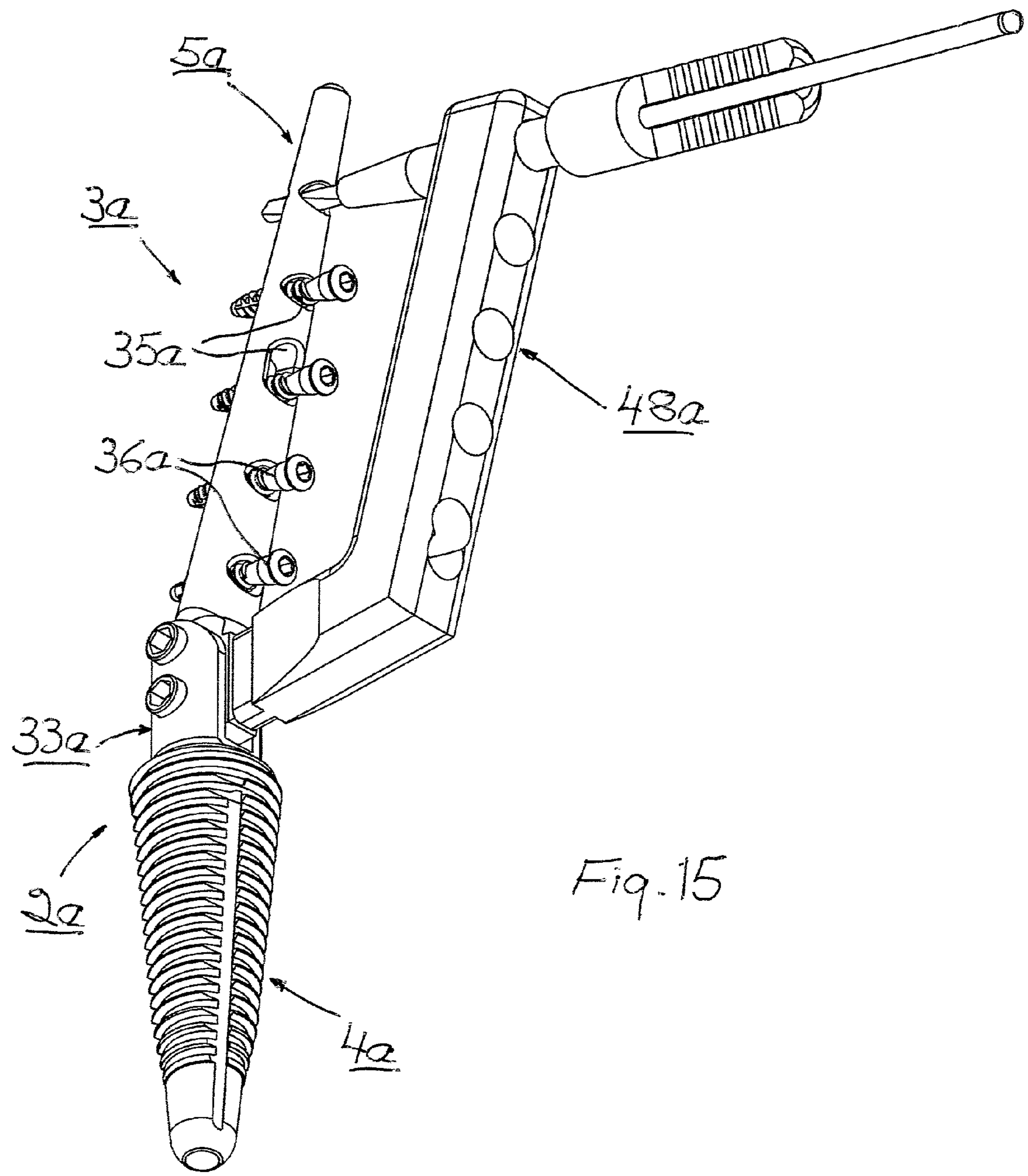
FIG. 15 illustrates schematically, except for the prosthesis, an instrument by means of which the attachment member with integrated lockable member is located in at least one bone.

In FIGS. 11 and 15, it is partly illustrated how the wrist prosthesis 1*a* is provided after the first attachment member 4*a* has been screwed into and attached to the radius 25*a*, alternatively after all members of an articulated prosthesis 1 according to FIG. 1 but the first attachment member 4 have been removed.

Thus, in FIG. 11 it is shown how the locking member 33*a* is located in the first attachment member 4*a* by inserting the attachment portion 16*a* of said locking member into the hole 8*a* in said attachment member and the locking member is tightened or secured by screwing in the hole by means of the attachment means 39*a* which, after it has been moved or screwed through the hole 38*a* in the attachment portion of the locking member, is brought to cooperate with the thread 14*a* in the hole 8*a* in said attachment member. The tightening by screwing of the attachment means 39*a* as described is performed by means of a screw tool of a suitable type. The locking member 33*a* is by rotation thereof brought to a suitable position in order to permit a suitable setting of the prosthesis in the medial-lateral plane before the locking member is fixed by tightening of the attachment means 39*a*. Accordingly, the attachment means 39*a* has two functions, namely to lock the locking member 33*a* axially to the first attachment member 4*a* and to lock the locking member to the first attachment member such that said locking member, after a suitable rotation there-of, no longer can rotate due to the friction caused by the axial pressure between the locking member and the attachment member.

After insertion of the second attachment member 5*a* with lockable member 34*a* in the drilled passage in the capitate 27*a* of carpus 26*a* and in the metacarpal bone 28*a*, the lockable portion 45*a* of the lockable member is fit in between the shanks 40*a* of the locking portion 37*a* of the locking member 33*a* and the lockable member is attached to the locking member by means of a screw 44*a* defining the pivoting axis, said screw being inserted into the holes 42*a*, 47*a* in said members. By means of the U-shaped configuration of the locking member 33*a* and the configuration of the lockable member 34*a* fitting thereto, these members may be provided or located separately and then assembled or mounted together without maximum stretching of the hand.

In FIG. 15 it is to a certain extent illustrated how the second attachment member 5*a* is fixed in the capitate and in the metacarpal bone. A first cortical screw 36*a* is screwed through the hole 35*a* shaped as a long-hole and locks the second attachment member 5*a* in the capitate 27*a* or the metacarpal bone 28*a*, depending on where the long-hole is situated, for possible necessary compression of the prosthesis 1*a*. After compression, additional cortical screws 36*a* are screwed into the remaining holes 35*a* in the second attachment member 5*a* and fix thereby said attachment member in the capitate and the metacarpal bone. During tightening of the cortical screws 36*a*, the guiding instrument illustrated in FIG. 14 may be used such that correct position of the screws relative to the holes 35*a* is reached before the screws are tightened. This because the holes 35*a* for the cortical screws 36*a* in the second attachment member 5*a* inside the capitate and the metacarpal bone can not be seen by the operating personnel.

After a suitable setting of the second attachment member 5*a* with the lockable member 34*a* relative to the first attachment member 4*a* and the locking member 33*a* for suitable setting of the prosthesis in the palmar-dorsal plane, the locking means 43*a* is inserted through the holes 41*a* in the shanks of the locking portion 37*a* of the locking member and through the long-hole 46*a* in the locking portion 45*a* of the lockable member 34*a* and is tightened for fixation of the lockable member to the locking member.

An alternative embodiment of the second attachment member 5*a* with the lockable member 34*a* according to the embodiment of FIGS. 7-14, is illustrated in FIGS. 16-19. Here, the second attachment member 5*b* with the lockable member 34*b* comprises an elongated and substantially plate-like member which is made in one piece, i.e. is integral with the lockable member 34*b*, and which is configured with holes 35*b* which extend transversely through said plate-like member and which are situated in line in the longitudinal direction thereof, said holes being provided for means 36*b* for attachment of said second attachment member to the capitate 27*b* of the carpus 26*b* and to the metacarpal bone 28*a*, i.e. to the outer side of said bones. In the illustrated embodiment, the second attachment member 5*b* has five holes 35*b* for attachment means 36*b*, of which the hole closest to the lockable member is angled relative to the other holes, because the plate-like second attachment member is made in one piece with the lockable member via an angular portion of the plate and a hole is provided in said portion. Said attachment means 36*b* consists of e.g. so called cortical screws. The attachment of the attachment means 36*b* is performed in substantially the same manner as at the embodiment of FIGS. 7-15. However, it is here possible to dispense with the instrument of FIG. 15, since the plate-like second attachment member 5*b*, contrary to the conically tapering second attachment member 5*a* according to FIGS. 7-10 and 14-15, extends outside the capitate 27*b* and the metacarpal bone 28*b*.

The other members of the wrist prosthesis 1*b* according to FIGS. 16-19 correspond with the wrist prosthesis of FIGS. 7-15 and the attachment is performed in a corresponding way.

The members of the wrist prosthesis 1*b* of FIGS. 16-19 have the same reference numerals as the corresponding members of the wrist prosthesis of FIGS. 7-15, but with the suffix "b" instead of the suffix "a".

The wrist prosthesis 1*c* according to FIGS. 20-24, which is somewhat modified in relation to the wrist prosthesis 1*a* according to FIGS. 7-15 and the wrist prosthesis 1*b* according to FIGS. 16-19, comprises a first prosthesis member 2*c* and a second prosthesis member 3*c*.

The first prosthesis member 2*c* comprises a first attachment member 4*c* and the second prosthesis member 3*c* a second attachment member 5*c*. The first prosthesis member 2*c* also comprises a locking member 33*c* instead of a socket member 6 and the second prosthesis member 3*c* a lockable member 34*c* instead of a head member 7. The first and second attachment members 4*c*, 5*c* are in the illustrated embodiment both shaped as screws, but may be shaped otherwise.

The first and second attachment members 4*c*, 5*c* are configured with a hole 8*c* and 9*c* respectively. The hole 8*c* in the first attachment member 4*c* has at least partly a conical shape and is at least partly configured with a thread 14*c*, like the holes 8, 8*a* and 8*b*. The hole 9*c* in the second attachment member 5*c* has at least partly a conical shape, like the hole 9.

The locking member 33*c* is configured with an attachment portion 16*c*, e.g. an attachment pin, which is insertable into the hole 8*c* in said first attachment member 4*c* for location of the locking member therein. Accordingly, the attachment portion 16*c* has a conically tapering outer side 17*c*. The shape and size of the attachment portion 16*c* and the shape and size of the hole 8*c* in the first attachment member 4*c* are chosen such that they, when pressed together, form a press fit, such that the locking member 33*c* and the first attachment member 4*c* can be brought to attach to each other by pressing said members together.

The lockable member 34*c* is configured with an attachment portion 19*c*, e.g. an attachment pin, which is insertable into the hole 9*c* in said second attachment member 5*c* for location of the locking member therein. Accordingly, the attachment portion 19*c* has a conically tapering outer side 20*c*. The shape and size of the attachment portion 19*c* and the shape and size of the hole 9*c* in the second attachment member 5*c* are chosen such that they, when pressed together in an axial direction, form a press fit, such that the lockable member 34*c* and the second attachment member 5*c* can be brought to attach to each other by pressing said members together.

The lockable member 34*c* is adjustably settable relative to the locking member 33*c* and in set position fixable to the locking member.

The locking member 33*c* and the lockable member 34*c* are, except that the lockable member in this embodiment is a separate member which is not integral with the second attachment member 5*c*, configured in a corresponding manner as the embodiments of FIGS. 7-15 and FIGS. 16-19.

Thus, except for the attachment portion 16*c*, the locking member 33*c* is also configured with a locking portion 37*c* which is connected to the attachment portion. The locking portion 37*c* is configured for fixation or attachment of the lockable member 34*c* thereto. The attachment portion 16*c* is configured with a hole 38*c* which extends through said attachment portion and in the longitudinal direction thereof for insertion therein of a partly threaded attachment means 39*c* for tightening or securing by screwing the locking member 33*c* to the first attachment member 4*c* by bringing said attachment means to cooperate with the threaded portion 14*c* of the hole 8*c* in said first attachment member. The locking portion 37*c* of the locking member 33*c* is in the illustrated embodiment substantially U-shaped and comprises two shanks 40*c* with holes 41*c*, 42*c* provided in said shanks opposite each other. Each shank 40*c* is in the illustrated embodiment configured with two holes 41*c*, 42*c* which extend through the shank and substantially in line in the longitudinal direction of the locking portion 37*c*. One hole 41*c* is configured for a locking means 43*c* (inclination screw) for fixation or attachment of the lockable member 34*c* to the locking member 33*c* and the other hole 42*c* is configured for an axis 44*c* about which the lockable member can pivot for adjustable setting thereof relative to the locking member.

Correspondingly, the lockable member 34*c* comprises in the illustrated embodiment a substantially flange-like lockable portion 45*c* for insertion between the shanks 40*c* of the locking portion 37*c* of the locking member 33*c*. The flange-like lockable portion 45*c* is configured with a curved long-hole 46*c*, which extends transversely therethrough, for said locking means 43*c* and with a hole 47*c*, also extending transversely through said lockable portion, for the axis 44*c* about which the lockable member can pivot for adjustable setting thereof relative to the locking member. At insertion of the flange-like lockable portion 45*c* between the shanks 40*c* of the locking portion 37*c* of the locking member 33*c*, portions of the long-hole 46*c* are brought in line with the holes 41*c* for the locking means 43*c* in said shanks for fixation or attachment of the lockable portion to the locking portion of the locking member and the hole 47*c* for the pivoting axis 44*c* is brought in line with the holes 42*c* for said pivoting axis in said shanks. The lockable portion 45*c* of the lockable member 34*c* may have another shape than the flange-like shape as long as it fulfils its function and permits insertion thereof between the shanks 40*c* of the locking portion 37*c* of the locking member 33*c*. The long-hole 46*c* in the lockable portion 45*c* of the lockable member 34*c* is configured with a plurality of, e.g. three fixed positions (see e.g. FIGS. 23 and 24) corresponding with different angular positions of the lockable member relative to the locking member.

The provision of the wrist prosthesis 1*c* is concluded after the first and second attachment members 4*c*, 5*c* have been screwed into and attached to the radius 25*c* and to the capitate 27*c* of the carpus 26*c* and the metacarpal bone 28*c* respectively, alternatively after all members of an articulated prosthesis 1 according to FIG. 1 but the first and second attachment members 4, 5 have been removed.

Thus, the locking member 33*c* is attached to the first attachment member 4*c* by inserting the attachment portion 16*c* of said locking member into the hole 8*c* in said attachment member and the locking member is tightened or secured by screwing in the hole by means of the attachment means 39*c* which, after it has been moved or screwed through the hole 38*c* in the attachment portion of the locking member, is brought to cooperate with the thread 14*c* in the hole 8*c* in said attachment member. The tightening by screwing of the attachment means 39*c* as described is performed by means of a screw tool of a suitable type. The locking member 33*c* is by rotation thereof brought to a suitable position in order to permit a suitable setting of the prosthesis in the medial-lateral plane before the locking member is fixed by tightening of the attachment means 39*c*. Accordingly, the attachment means 39*c* has also in this embodiment two functions, namely to lock the locking member 33*c* axially to the first attachment member 4*c* and to lock the locking member to the first attachment member such that said locking member, after a suitable rotation thereof, no longer can rotate due to the friction caused by the axial pressure between the locking member and the attachment member.

The lockable member 34*c* is located in the second attachment member 5*c* by inserting the attachment portion 19*c* of said locking member into the hole 9*c* in said attachment member. After the insertion, the lockable portion 45*c* of the lockable member 34*c* is fit in between the shanks 40*c* of the locking portion 37*c* of the locking member 33*c* and the lockable member is attached to the locking member by means of a screw 44*c* defining the pivoting axis, said screw being inserted into the holes 42*c*, 47*c* in said members.

After a suitable setting of the second attachment member 5*c* with the lockable member 34*c* relative to the first attachment member 4*c* and the locking member 33*c* for suitable setting of the prosthesis in the palmar-dorsal plane, the locking means 43*c* is inserted through the holes 41*c* in the shanks of the locking portion 37*c* of the locking member and through the long-hole 46*c* in the locking portion 45*c* of the lockable member 34*c* and is tightened for fixation of the lockable member to the locking member.

The finger joint prosthesis 1*d* according to FIGS. 25-28 is somewhat modified in relation to the wrist prosthesis 1*c* according to FIGS. 20-24, but comprises like said wrist prosthesis a first prosthesis member 2*d* and a second prosthesis member 3*d*. Even if the prosthesis in the illustrated embodiment is configured for a finger joint, the illustrated embodiment is in principal also applicable to wrist prostheses. The first prosthesis member 2*d* comprises a first attachment member 4*d* and the second prosthesis member 3*d* a second attachment member 5*d*. The first prosthesis member 2*d* also comprises a locking member 33*d* instead of a socket member 6 and the second prosthesis member 3*d* a lockable member 34*d* instead of a head member 7. The first and second attachment members 4*d*, 5*d* are in the illustrated embodiment both shaped as screws and also somewhat shorter since it is a finger joint prosthesis, but may be shaped otherwise for other applications, e.g. be a little bit longer as at the illustrated wrist prostheses.

The first and second attachment members 4*d*, 5*d* are each configured with a hole 8*d* and 9*d* respectively. The hole 8*d* in the first attachment member 4*d* has at least partly a conical shape and is at least partly configured with a thread 14*d*, like the holes 8, 8*a*, 8*b* and 8*c*. The hole 9*d* in the second attachment member 5*d* has at least partly a conical shape, like the hole 9 and 9*c*, and is partly configured with a thread 48*d*.

The locking member 33*d* is configured with an attachment portion 16*d*, e.g. an attachment pin, which is insertable into the hole 8*d* in said first attachment member 4*d* for location of the locking member therein. Accordingly, the attachment portion 16*d* has a conically tapering outer side 17*d*. The shape and size of the attachment portion 16*d* and the shape and size of the hole 8*d* in the first attachment member 4*d* are chosen such that they, when pressed together in an axial direction, form a press fit, such that the locking member 33*d* and the first attachment member 4*d* can be brought to attach to each other by pressing said members together.

The lockable member 34*d* is configured with an attachment portion 19*d*, e.g. an attachment pin, which is insertable into the hole 9*d* in said second attachment member 5*d* for location of the locking member therein. Accordingly, the attachment portion 19*d* has a conically tapering outer side 20*d*. The shape and size of the attachment portion 19*d* and the shape and size of the hole 9*d* in the second attachment member 5*d* are chosen such that they, when pressed together in an axial direction, form a press fit, such that the lockable member 34*d* and the second attachment member 5*d* can be brought to attach to each other by pressing said members together.

The lockable member 34*d* is adjustably settable relative to the locking member 33*d* and in set position fixable to the locking member.

The locking member 33*d* and the lockable member 34*d* are in this embodiment both configured as separate members, i.e. not made in one piece with the first and second attachment members 4*d*, 5*d* respectively, and are also configured differently from the embodiments of FIGS. 7-15, 16-19 and 20-24.

Thus, except for the attachment portion 16*d*, the locking member 33*d* is configured with a locking portion 37*d* which is connected to the attachment portion. The locking portion 37*d* is configured for fixation or attachment of the lockable member 34*d* thereto. The attachment portion 16*d* is configured with a hole 38*d* which extends through said attachment portion and in the longitudinal direction thereof for insertion therein of a partly threaded attachment means 39*d* for tightening or securing by screwing the locking member 33*d* to the first attachment member 4*d* by bringing said attachment means to cooperate with the threaded portion 14*d* of the hole 8*d* in said first attachment member. The locking portion 37*d* of the locking member 33*d* is in the illustrated embodiment configured substantially as a hemisphere with radially extending furrows or grooves 49*d* on a base or bottom surface thereof and with a hole 50*d* extending perpendicular to the hole 38*d* and provided for a locking means 43*d* (inclination screw) for fixation or attachment of the lockable member 34*d* to the locking member 33*d*, said locking means defining an axis about which the lockable member can pivot for adjustable setting thereof relative to the locking member.

Correspondingly, the lockable member 34*d* comprises, except for the attachment portion 19*d* which in comparison with the locking member 33*d* is somewhat longer, a lockable portion 45*d* which is connected to the attachment portion and configured for fixation or attachment to the locking member 33*d*. The attachment portion 19*d* is configured with a hole 51*d* which extends through said attachment portion and in the longitudinal direction thereof for insertion therein of a partly threaded attachment means 52*d* for tightening or securing by screwing the lockable member 34*d* to the second attachment member 5*d* by bringing said attachment means to cooperate with the threaded portion 48*d* of the hole 9*d* in said second attachment member. The lockable portion 45*d* of the lockable member 34*d* is in the illustrated embodiment shaped substantially as a hemisphere with radially extending furrows or grooves 53*d* on a base or bottom surface thereof and with a hole 54*d* which extends perpendicular to the hole 51*d* and which when attaching the locking member 33*d* and the lockable member 34*d* to each other is brought in line with the hole 50*d* in the locking member 33*d* for cooperation with the locking means 43*d*. During assembly of the locking member 33*d* and the lockable member 34*d*, the furrows or grooves 49*d*, 53*d* on the locking portion 37*d* of the locking member 33*d* and on the lockable portion 45*d* of the lockable member 34*d* respectively, are also brought into engagement with each other for setting of different angular positions of the lockable member relative to the locking member. After assembly at the desired angular position, the members 33*d*, 34*d* are fixed to each other by means of the locking means 43*d*. The shape, number and arrangement of the furrows or grooves 49*d*, 53*d* may of course vary as long as they fulfill their function and permit cooperation with each other. It is however obvious that the setting possibilities vary with the number of furrows or grooves 49*d*, 53*d* on the locking member 33*d* and the lockable member 34*d* respectively.

The provision of the finger joint prosthesis 1*d* is concluded after the first and second attachment members 4*d*, 5*d* have been screwed into and attached to the respective bone in the finger, alternatively after all members of an articulated prosthesis except the first and second attachment members 4, 5 have been removed.

Thus, the locking member 33*d* is attached to the first attachment member 4*d* by inserting the attachment portion 16*d* of said locking member into the hole 8*d* in said attachment member and the locking member is tightened or secured by screwing in the hole by means of the attachment means 39*d* which, after it has been moved or screwed through the hole 38*d* in the attachment portion of the locking member, is brought to cooperate with the thread 14*d* in the hole 8*d* in said attachment member. The tightening by screwing of the attachment means 39*d* is performed by means of a screw tool of a suitable type. For wrist applications, the locking member 33*d* is by rotation thereof brought to a suitable position in order to permit a suitable setting of the prosthesis in the medial-lateral plane before the locking member is fixed by tightening of the attachment means 39*d*. Accordingly, the attachment means 39*d* has also here two functions, namely to lock the locking member 33*d* axially to the first attachment member 4*d* and to lock the locking member to the first attachment member such that said locking member, after a suitable rotation thereof, no longer can rotate due to the friction caused by the axial pressure between the locking member and the attachment member.

The lockable member 34*d* is attached to the second attachment member 5*d* by inserting the attachment portion 19*d* of said lockable member into the hole 9*d* in said attachment member and the lockable member is tightened or secured by screwing in the hole by means of the attachment means 52*d* which, after it has been moved or screwed through the hole 51*d* in the attachment portion of the lockable member, is brought to cooperate with the thread 48*d* in the hole 9*d* in said attachment member. The tightening by screwing of the attachment means 52*d* is performed by means of a screw tool of a suitable type. After insertion, the lockable portion 45*d* of the lockable member 34*d* is assembled with or attached to the locking portion 37*d* of the locking member 33*d* as described above.

After a suitable setting of the second attachment member 5*d* and the lockable member 34*d* relative to the first attachment member 4*d* and the locking member 33*d* for suitable setting of the prosthesis in the palmar-dorsal plane, the locking means 43*d* is inserted through the hole 50*d* in the locking portion 37*d* of the locking member and through the hole 54*d* in the locking portion 45*d* of the lockable member and is tightened for fixation of the lockable member to the locking member.

The prostheses 1*a*, 1 b, 1*c* and 1*d* and the members forming part thereof can be manufactured of e.g. a suitable titanium alloy, such as Ti6Al4V, since this will facilitate ingrowth of bone tissue into and around the prosthesis. At the prosthesis 1*b*, the substantially plate-like second attachment member 5*b* with the lockable member 34*b* may consist of a suitable steel for implants.

Except that a prosthesis according to the invention has a simple construction and is easy to position, it also provides for a small incision and that only smaller parts of the respective bone have to be cut away for attachment of the first and second attachment members.

By means of the first and possibly also the second attachment member, it is possible when required, also during surgery, to decide if the joint shall be replaced (artroplasty) or the joint shall be made rigid (primary artrodhesis) and it is possible to later, if required, perform an artrodhesis and thereby use parts of the prosthesis for replacement of the joint, or even by means of parts of the prosthesis for an artrodhesis see to that the joint again can be articulated. The setting possibilities of the prosthesis for artrodhesis is extensive in the medial-lateral as well as in the palmar-dorsal plane.

The invention is not limited to the embodiments described above and illustrated in the drawings, but may vary within the scope of the subsequent claims without departing from the idea and purpose of the invention. Thus, the prosthesis members may be used at other smaller joints than wrists, e.g. at finger and toe or interphalangeal joints, pollex joints and cubital joints. The design of the prosthesis members may also vary. Thus, the holes in the first and second attachment members possibly have another shape than conical shape and the socket and head members, alternatively the locking member and the lockable member, are of course adapted thereto. The press fit may be another type of coupling device. Socket and head, alternatively the locking member and lockable member, may be shaped otherwise than shown. The screw tool may also be of another suitable type than a screwdriver.

The invention claimed is:

1. A joint prosthesis for attachment to bones at a joint, comprising:

two prosthesis members (2*a,* 3*a*; 2*b,* 3*b*) which each is configured for attachment thereof to at least one of the bones at the joint, wherein one of the prosthesis members (2*a*; 2*b*) comprises a first attachment member (4*a*; 4*b*) which is configured for attachment to at least one of the bones at the joint, the other prosthesis member (3*a*; 3*b*) including a second attachment member (5*a*; 5*b*) which is configured for attachment to at least one other bone at the joint, wherein said one prosthesis member (2*a*; 2*b*) comprises a locking member (33*a*; 33*b*) and said other prosthesis member (3*a*; 3*b*) a lockable member (34*a*; 34*b*), wherein the locking member (33*a*; 33*b*) is configured with an attachment portion (16*a;*16*b*) which is insertable into a hole (8*a;* 8*b*) in said first attachment member (4*a*; 4*b*) for attachment or location of the locking member therein, wherein except for the attachment portion (16*a*; 16*b*) the locking member (33*a*; 33*b*) is also configured with a locking portion (37*a*; 37*b*) which is connected to the attachment portion and configured for fixation or attachment of the lockable member (34*a*; 34*b*) thereto, and wherein the attachment portion (16*a*; 16*b*) is configured with a hole (38*a*; 38*b*) which extends through said attachment portion and in the longitudinal direction thereof for insertion therein of a partly threaded attachment means (39*a*; 39*b*) for tightening or securing by screwing the locking member (33*a*; 33*b*) to the first attachment member (4*a*; 4*b*) by bringing said attachment means to cooperate with a threaded portion (14*a*; 14*b*) of the hole (8*a*; 8*b*) in said first attachment member, wherein the locking portion (37*a*; 37*b*) of the locking member (33*a*; 33*b*) is substantially U-shaped and comprises two shanks (40*a;* 40*b*) with two holes (41*a,* 42*a;* 41*b,* 42*b*) provided in each shank (40*a*; 40*b*) opposite each other and substantially in line in the longitudinal direction of the locking portion (37*a*; 37*b*), whereby one hole (41*a*; 41*b*) is configured for a locking means (43*a*; 43*b*) for fixation or attachment of the lockable member (34*a*; 34*b*) to the locking member (33*a*; 33*b*) and whereby the other hole (42*a*; 42*b*) is configured for a pivoting axis member (44*a*; 44*b*) about which the lockable member can pivot for adjustable setting thereof relative to the locking member, wherein the lockable member (34*a*; 34*b*) is made in one piece with the second attachment member (5*a*; 5*b*), wherein the lockable member (34*a*; 34*b*) comprises a lockable portion (45*a*; 45*b*) which is configured for insertion between the shanks (40*a*; 40*b*) of the locking portion (37*a*; 37*b*) of the locking member (33*a*; 33*b*), wherein the lockable portion (45*a*; 45*b*) is configured with a curved long-hole (46*a*; 46*b*) for said locking means (43*a*; 43*b*) that extends transversely therethrough, and with a hole (47*a*; 47*b*), also extending transversely through said lockable portion, for the pivoting axis member (44*a*; 44*b*) about which the lockable member (34*a*; 34*b*) can pivot for adjustable setting thereof relative to the locking member, and wherein at insertion of the lockable portion (45*a*; 45*b*) between the shanks (40*a*; 40*b*) of the locking portion (37*a*; 37*b*) of the locking member (33*a*; 33*b*), portions of the long-hole (46*a*; 46*b*) are brought in line with the holes (41*a*; 41*b*) in said shanks to allow the locking means (43*a*; 43*b*) to pass through the long-hole (46*a*; 46*b*) and the holes (41*a*; 41*b*) for fixation or attachment of the lockable portion to the locking portion of the locking member and the hole (47*a*; 47*b*) for the pivoting axis member (44*a*; 44*b*) is brought in line with the holes (42*a*; 42*b*) for said pivoting axis member (44*a*; 44*b*) in said shanks, wherein the long-hole (46*a*; 46*b*) in the lockable portion (45*a*; 45*b*) of the lockable member (34*a*; 34*b*) is configured with a plurality of fixed positions corresponding to different angular positions of the lockable member relative to the locking member (33*a*; 33*b*) for fixation of the lockable member in any of said angular positions, wherein the prosthesis (1*a*; 1*b*) further comprises said pivoting axis member (44*a*; 44*b*) and said locking means (43*a*; 43*b*), and wherein the prosthesis (1*a*; 1*b*) is configured for arthrodesis of wrists (24*a*; 24*b*), whereby one prosthesis member (2*a*; 2*b*) is configured for attachment to the radius (25*a*; 25*b*) and the other prosthesis member (3*a*; 3*b*) for attachment to one of the bones (27*a*; 27*b*) of the carpus (26*a*; 26*b*) and a metacarpal bone (28*a;* 28*b*).

2. Prosthesis according to claim 1, wherein the second attachment member (5*a*) comprises an elongated, from the lockable member (34*a*) substantially conically tapering member with transverse through said member extending, substantially in line in the longitudinal direction of said member configured holes (35*a*) for means (36*a*) for fixation or attachment of said second attachment member in said at least one other bone.

3. Prosthesis according to claim 1, wherein the second attachment member (5*b*) comprises an elongated, substantially plate-like member with transverse through said member extending, substantially in line in the longitudinal direction of said member configured holes (35*b*) for means (36*b*) for fixation or attachment of said second attachment member at said at least one other bone.

4. Prosthesis according to claim 1, wherein the attachment portion (16*a*; 16*b*) of the locking member (33*a*; 33*b*) is configured to define a press fit with the hole (8*a*; 8*b*) in said first attachment member (4*a*; 4*b*).

5. Prosthesis according to claim 4, wherein the attachment portion (16*a*; 16*b*) of the locking member (33*a*; 33*b*) has a conical shape, and wherein the hole (8*a*; 8*b*) in said first attachment member (4*a*; 4*b*) has a conical shape.

6. Prosthesis according to claim 1, wherein the prosthesis member (2*a*; 2*b*) which is configured for attachment to the radius (25*a*; 25*b*) comprises said first attachment member (4*a*; 4*b*).

7. Prosthesis according to claim 6, wherein said first attachment member (4*a*; 4*b*) substantially screw-like.

8. Prosthesis according to claim 7, wherein said first attachment member (4*a*; 4*b*) comprises the screw-like attachment member of a prosthesis member for an articulated joint prosthesis which is configured for attachment by screwing in the radius (25*a*; 25*b*), where a part of the hole (8; 8*a*; 8*b*) in the attachment member has a conical shape for attachment by means of a press fit in said hole of a socket member (6).

9. Prosthesis according to claim 1, wherein the prosthesis member (3*a*; 3*b*) which is configured for attachment to one of the bones (27*a*; 27*b*) of the carpus (26*a*; 26*b*) and a metacarpal bone (28*a*; 28*b*) comprises said second attachment member (5*a*; 5*b*).

10. Prosthesis according to claim 1, wherein the perimeter of the long-hole is defined by a plurality of shapes, with each shape being configured to receive the locking means to fix the lockable member in a different angular position relative to the locking member.

11. Prosthesis according to claim 10, wherein the plurality of shapes comprises overlapping circles.

12. Prosthesis according to claim 1, wherein a centerline of the long-hole passes through each of the fixed positions and extends along an arc centered on the axis about which the lockable member pivots.

* * * * *